(12) United States Patent
Holmberg et al.

(10) Patent No.: US 11,136,331 B2
(45) Date of Patent: Oct. 5, 2021

(54) METHODS OF O-DEMETHYLATION

(71) Applicant: Cambrex Charles City, Inc., Charles City, IA (US)

(72) Inventors: Par Holmberg, Charles City, IA (US);
Lars Eklund, Charles City, IA (US);
David Adams, Charles City, IA (US);
Michael Letourneau, Charles City, IA (US); Margus Eek, Charles City, IA (US); Alo Soone, Charles City, IA (US)

(73) Assignee: CAMBREX CHARLES CITY, INC., Charles City, IA (US)

( * ) Notice: Subject to any disclaimer, the term of this patent is extended or adjusted under 35 U.S.C. 154(b) by 1 day.

(21) Appl. No.: 16/755,719

(22) PCT Filed: Oct. 12, 2018

(86) PCT No.: PCT/GB2018/052929
§ 371 (c)(1),
(2) Date: Apr. 13, 2020

(87) PCT Pub. No.: WO2019/073247
PCT Pub. Date: Apr. 18, 2019

(65) Prior Publication Data
US 2021/0188862 A1    Jun. 24, 2021

(30) Foreign Application Priority Data
Oct. 13, 2017    (GB) ..................... 1716830

(51) Int. Cl.
*C07D 489/12*    (2006.01)
*A61K 31/485*    (2006.01)

(52) U.S. Cl.
CPC ................. *C07D 489/12* (2013.01)

(58) Field of Classification Search
CPC ..................... C07D 489/12; A61K 31/485
USPC ............................... 546/39; 514/485
See application file for complete search history.

(56) References Cited

U.S. PATENT DOCUMENTS

| 6,291,675 | B1 | 9/2001 | Coop |
| 6,395,900 | B1 | 5/2002 | Coop |
| 8,232,397 | B2 | 7/2012 | Allen |

FOREIGN PATENT DOCUMENTS

| EP | 2332410 | 6/2011 |
| WO | 9744317 | 11/1997 |
| WO | 2007061828 | 5/2007 |
| WO | 2009/114118 | 9/2009 |
| WO | 2009114118 | 9/2009 |
| WO | 2010039220 | 4/2010 |
| WO | 2013/007986 | 1/2013 |
| WO | 2013007986 | 1/2013 |
| WO | 2013/088254 | 6/2013 |
| WO | 2013088254 | 6/2013 |
| WO | 2015171354 | 11/2015 |

OTHER PUBLICATIONS

Bentley, et al., "Novel analgesics and molecular rearrangements in the morphine-thebaine group. III. Alcohols of the 6,14-endo-ethenotetrahydrooripavine series and derived analogs of N-allylnormorphine and -norcodeine", J. am. Chem. Soc., 89(13):3281-3292 (1967).
Coop, et al., "Direct and Simple O-Demethylation of Thebaine to Oripavine", J. Org. Chem., 61:6774 (1996).
Coop, et al., "L-Selectride as a General Reagent for the O-Demethylation and N-Decarbomethoxylation of Opium Alkaloids and Derivatives", J. Org. Chem., 63:4392-4396 (1998).
Gartner, et al., "Lithium tri-sec-butylborodeuteride: a new reagent for the stereoselective deuterium addition to cyclohexanones with single chair conformations", Arkivoic (ii):9-20(2001).
Hubbard, "Lithium Tri-sec-butylborohydride", Encyclopedia of Reagents for Organic Synthesis L-Selectride, 1-6 (2001).
Hudlicky, et al., "Recent advances in process development for opiate-derived pharmaceutical agents", Can. J. Chem., 93:492-501 (2015).
International Search Report for corresponding PCT application PCT/GB2018/052929 dated Jan. 21, 2019.
Kabalka, "A Mild and Convenient Oxidation Procedure for the Conversion of Organoboranes to the Corresponding Alcohols", J. Org. Chem., 40(12): 1776-1779 (1975).
Majetich, et al., "Hydride-promoted demethylation of methyl phenyl ethers", Tetrahedron Lett., 35:8727-8730 (1994).
Marton, et al., "Design and Synthesis of an 18F-Labeled Version of Phenylethyl Orvinol ([18F]FE-PEO) for PET-Imaging of Opioid Receptors", Molecules, 17:11554-11569 (2012).
Marton, et al., "Herstellung von 6, 14-Ethenomorphinan-Derivaten", Chemical Monthly, 125(11):1229-1239 (1994).
Tuckmantel, et al., "Studies in Polyphenol Chemistry and Bioactivity. 1. Preparation of Building Blocks from (+)-Catechin. Procyanidin Formation. Synthesis of the Cancer Cell Growth Inhibitor, 3-O-Galloyl-(2R,3R)-epicatechin-4â,8-[3-O-galloyl-(2R,3R)-epicatechin]", J. Am. Chem. Soc., 121:12073-12081 (1999).

(Continued)

Primary Examiner — Charanjit Aulakh
(74) Attorney, Agent, or Firm — Pabst Patent Group LLP

(57) ABSTRACT

There is provided a novel process for the preparation of a compound of formula I,

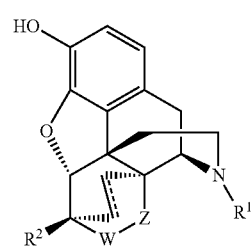

wherein $R^1$, $R^2$, W, Z and ⫽ are as described in the description, by demethylation of a corresponding O-methyl derivative with a borohydride-based reagent. This process may be used in the preparation of buprenorphine.

19 Claims, No Drawings

(56) References Cited

OTHER PUBLICATIONS

Waser, et al., "Process Development for a Key Synthetic Intermediate of LY2140023, a Clinical Candidate for the Treatment of Schizophrenia", Org. Process Res. Dev., 15:1266-1274 (2011).
Wu, et al., "Position of Coordination of the Lithium Ion Determines the Regioselectivity of Demethylations of 3,4-Dimethoxymorphinans with L-Selectride", Org. Lett., 7:2531-2534 (2005).
Zweifel, et al., "Hydration of Olefins, Dienes, and Acetylenes via Hyrdoboration", Organic Reactions, 1:1-54 (1963).

METHODS OF O-DEMETHYLATION

CROSS-REFERENCE TO RELATED APPLICATIONS

This application is a National Phase application under 35 U.S.C. § 371 of International Application No. PCT/GB2018/052929, filed Oct. 12, 2018, entitled "NEW PROCESS," by Par HOLMBERG; Lars EKLUND; David ADAMS; Michael LETOURNEAU; Margus EEK; and Alo SOONE, which claims the benefit of and priority to U.K. Application No. GB1716830.3 filed Oct. 13, 2017, which are hereby incorporated herein by reference in their entirety.

FIELD OF THE INVENTION

The present invention relates to a new demethylation process that is useful in the synthesis of certain semi synthetic opioids/alkaloids (including opioid receptor agonists, antagonists and other derivatives thereof) and/or intermediates thereto. In particular, the invention relates to new processes for modifying semi synthetic opioids/alkaloids that are structurally related to morphine.

BACKGROUND OF THE INVENTION

Thevinols and orvinols are classes of semi-synthetic derivatives of thebaine and oripavine, respectively, first developed in the 1960s. Orvinols (1) may be synthesized by a multi-step process, starting with a Diels-Alder reaction between thebaine (2) and an appropriate dienophile (3) to provide the corresponding thevinol (4). Subsequent 3-O-demethylation yields the corresponding orvinol (Scheme 1).

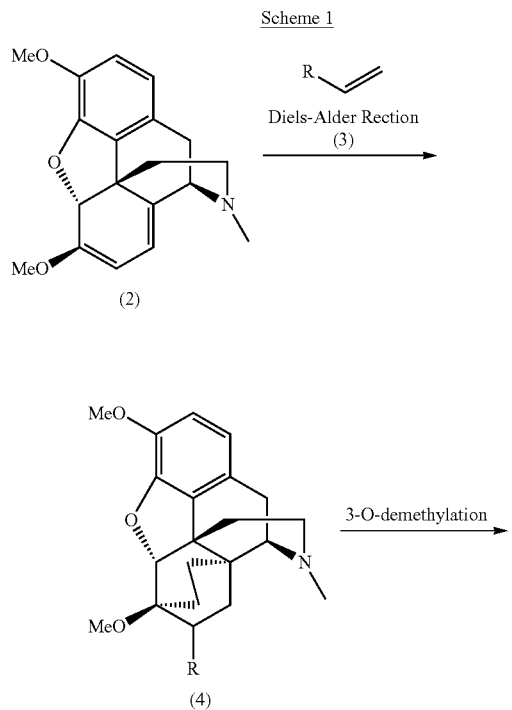

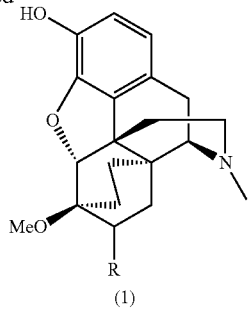

Thebaine itself has no medicinal use, but is a relatively abundant and naturally occurring opioid, and is a useful starting material in the synthesis of many opiate derivatives. Thebaine features a 3-methyl phenyl ether, and a key step in the manufacture of many semi synthetic opioids involves the O-demethylation of this group to provide the corresponding 3-phenol.

The orvinols are extremely potent p-opioid agonists, and a particularly important member of this class is buprenorphine. Buprenorphine is a semi synthetic opioid derivative of thebaine, and is used in the treatment of opiate addiction, pain and depression.

Thebaine and derivatives thereof, including buprenorphine, possess the morphinan core structure (5), and the atom numbering of these compounds follows the established convention for this structure as shown below.

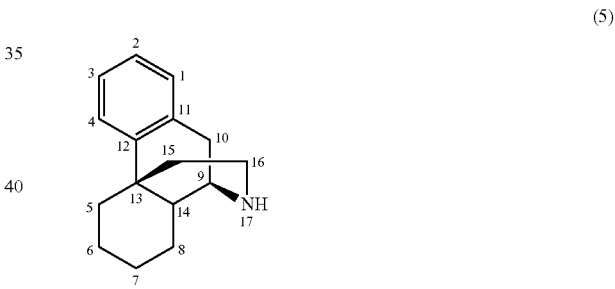

Traditionally, the synthesis of buprenorphine involves a 3-O-demethylation step that is achieved using potassium hydroxide at 200° C. See, for example, K. Bentley et. al., *J. Am. Chem. Soc.*, 1967, 89, 3281-3292 and U.S. Pat. No. 8,232,397. However, it is found that the extremely high temperature and strongly alkaline environment results in relatively a low yield (60% to 70%) of an impure product. The impurities produced are often structurally related to buprenorphine and are difficult to remove. Furthermore, such harsh conditions are of limited use when applied to industrial processes. For example, specialised heating equipment and reactors are usually required.

G. Majetich, et al., *Tetrahedron Lett.* 1994, 35, 8727-8730 discusses the use of L-Selectride® as a demethylation agent in the conversion of methyl phenyl ethers to the corresponding phenols. However, there is no discussion of the use of this methodology with opioids.

U.S. Pat. Nos. 6,291,675 and 6,395,900 and articles A. Coop, et al., *J. Org. Chem.*, 1996, 61, 6774 and A. Coop, et al., *J. Org. Chem.*, 1998, 63, 4392-4396 disclose processes wherein L-Selectride® is used in the 3-O-demethylation of certain morphinan derivatives. However, the processes are unsuitable for commercial scale manufacturing of morphinan derivatives since they can be slow (with reaction times of up to 14 days) and relatively inefficient (isolated yields averaging around 65%). It is important to minimise the formation of structurally related impurities in these processes, particularly when the processes are involved in the formation of active pharmaceutical ingredients for administration to patients, in order to avoid costly and time-consuming purification procedures, which may not be economically feasible on a manufacturing scale.

More recently, H. Wu et al., *Org. Lett.*, 2005, 7, 2531-2534 discusses the regioselectivity of using L-Selectride® in the demethylation of certain morphinan derivatives. However, the reaction requires a relatively large quantity of L-Selectride®.

The present invention addresses some of the problems associated with the processes of the prior art. Particularly, the inventors have surprisingly found that certain additives can greatly improve the 3-O-demethylation reaction efficiency when they are used with certain morphinan derivatives.

The listing or discussion of an apparently prior-published document in this specification should not necessarily be taken as an acknowledgement that the document is part of the state of the art or common general knowledge.

DISCLOSURE OF THE INVENTION

According to a first aspect of the present invention, there is provided a process for the preparation of a compound of formula I,

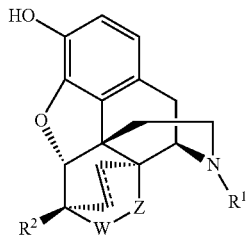

or a pharmaceutically acceptable salt thereof;
wherein:
W and Z independently represent $CHR^3$ or S, provided that at least one of W and Z represents $CHR^3$;
$R^1$ represents hydrogen, $C_{1-12}$ alkyl, $C_{2-12}$ alkenyl, $C_{2-12}$ alkynyl or $C_{3-12}$ cycloalkyl (which latter four groups are optionally substituted by one or more substituents selected from the list consisting of halogen atoms, phenyl groups and $C_{3-12}$ cycloalkyl groups);
$R^2$ represents hydrogen, a halogen atom, —$OR^4$, —OC(O)$R^4$, —$N(R^4)_2$, $C_{1-12}$ alkyl, $C_{2-12}$ alkenyl or $C_{2-12}$ alkynyl (which latter three groups are optionally substituted by one or more halogen atoms);
each $R^3$ independently represents hydrogen, —CN, $C_{1-12}$ alkyl, $C_{2-12}$ alkenyl, $C_{2-12}$ alkynyl or $C_{3-12}$ cycloalkyl (which latter four groups are optionally substituted by one or more substituents selected from the list consisting of halogen atoms, —$OR^5$ groups and 5 to 10-membered heteroaryl groups);
$R^4$ independently represents hydrogen, $C_{1-6}$ alkyl, $C_{3-6}$ cycloalkyl, $C_{6-10}$ aryl (which latter three groups are optionally substituted by one or more substituents selected from the list consisting of halogen atoms and phenyl groups);

$R^5$ represents hydrogen or $C_{1-6}$ alkyl optionally substituted by one or more halogen atoms; and
⟍ represents a single or double bond;
which process comprises contacting a compound of formula II,

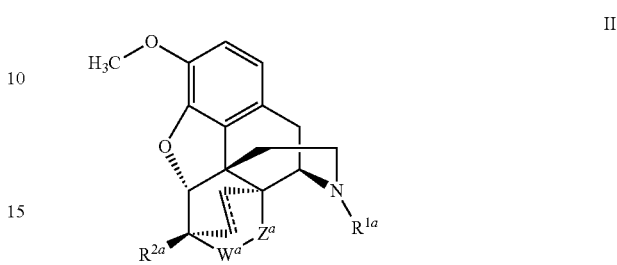

or a salt thereof wherein $R^{1a}$, $R^{2a}$, $W^a$ and $Z^a$ are defined according to $R^1$, $R^2$, W and Z, respectively, with an alkali metal borohydride and an additional alkali metal salt;
which process is hereinafter referred to as "the process of the invention".

The process of the invention may be performed employing salts or solvates (of compounds of formula II), and may produce compounds that are in the form of a (e.g. corresponding) salt or solvate (of compounds of formula I). Particular salts that may be mentioned include organic acid salts such as tartrate salts (e.g. bitartrate salts) and inorganic acid salts such as hydrohalide salts (e.g. hydrochloride salts). However, in certain embodiments of the invention, the process of the invention is performed using the free base of the compound of formula II.

Compounds employed in or produced by the processes described herein (i.e. those involved in the process of the invention) may exhibit tautomerism. The process of the invention therefore encompasses the use or production of such compounds in any of their tautomeric forms, or in mixtures of any such forms.

Unless otherwise specified, alkyl groups, alkenyl groups and alkynyl groups as defined herein may be straight-chain or, when there is a sufficient number (i.e. a minimum of three) of carbon atoms be branched-chain. Cycloalkyl groups may be fully or partly cyclic (for example, a $C_4$ cycloalkyl group may be a —$CH_2$-cyclopropyl group).

Further, the compounds employed in or produced by the processes described herein may contain double bonds and may thus exist as E (entgegen) and Z (zusammen) geometric isomers about each individual double bond. All such isomers and mixtures thereof are included within the scope of the invention.

The term "aryl", when used herein, includes $C_{6-10}$ aryl groups. Such groups may be monocyclic or bicyclic and, when bicyclic, be either wholly or partly aromatic. $C_{6-10}$ aryl groups that may be mentioned include phenyl, naphthyl, indenyl, and the like. For the avoidance of doubt, the point of attachment of substituents on aryl groups may be via any carbon atom of the ring system.

Unless otherwise specified, the term "heteroaryl" or "heteroaromatic", when used herein, refers to an aromatic group containing one or more heteroatom(s) (e.g. one to four heteroatoms) preferably selected from N, O and S. Heteroaryl groups include those which have from 5 to 10 members (e.g. from 5 to 7) and may be monocyclic or bicyclic, provided that at least one of the rings is aromatic (so forming, for example, a mono- or bicyclic heteroaromatic group). When the heteroaryl group is bicyclic the point of attachment may be via any atom including an atom of a non-aromatic ring. However, when heteroaryl groups are bicyclic, they are preferably linked to the rest of the molecule via an aromatic ring. Heteroaryl groups that may be mentioned include benzofuranyl, furanyl, imidazolyl, indolyl, isoquinolinyl, oxazolyl, pyrazinyl, pyrazolyl, pyridazinyl, pyridyl, pyrimidinyl, pyrrolyl, quinolinyl, tetrahydroquinolinyl, thiazolyl and thienyl. Substituents on heteroaryl groups may, where appropriate, be located on any atom in the ring system including a heteroatom. The point of attachment of heteroaryl groups may be via any atom in the ring system including (where appropriate) a heteroatom (such as a nitrogen atom). Heteroaryl groups may also be in the N- or S-oxidised form.

For the avoidance of doubt, the term "bicyclic" (e.g. when employed in the context of aryl and heteroaryl groups) refers to groups in which the second ring of a two-ring system is formed between two adjacent atoms of the first ring.

The terms "halo", "halogen" and "halide", when used herein, include fluoro, chloro, bromo and iodo.

The term "about", when used herein, when referring to a measurable value (such as an amount of a particular component in the reaction mixture), refers to variations of ±20%, ±10%, ±5%, ±1%, ±0.5%, or ±0.1% of the specified amount.

We also disclose compounds of formula I in which W and Z independently represent $CHR^3$ or S.

In particular embodiments of the invention, $R^1$ in the compound of formula I represents hydrogen, $C_{1-6}$ alkyl, $C_{2-6}$ alkenyl, $C_{2-6}$ alkynyl or $C_{3-6}$ cycloalkyl, (which latter four groups are optionally substituted by one or more substituents selected from the list consisting of halogen atoms, phenyl groups and $C_{3-6}$ cycloalkyl groups). In other particular embodiments, $R^1$ represents hydrogen, $C_{1-6}$ alkyl or $C_{3-6}$ cycloalkyl (which latter two groups are optionally substituted by one or more substituents selected from the list consisting of halogen atoms, phenyl groups and $C_{3-6}$ cycloalkyl groups). In further particular embodiments, $R^1$ represents methyl, ethyl, propyl, butyl, benzyl, or —$CH_2$-cyclopropyl. In preferred embodiments, $R^1$ represents —$CH_2$-cyclopropyl.

In particular embodiments of the invention, W and Z in the compound of formula I independently represent $CHR^3$. For example, W may represent $CHR^3$ and Z may represent $CH_2$. Thus, further compounds of interest that may be mentioned include those of formula IA,

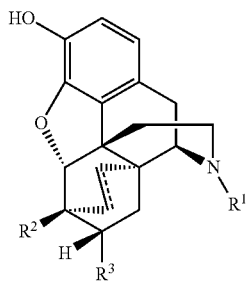

IA in which $R^1$, $R^2$ and $R^3$ are as defined above.

In particular embodiments, one of W and Z represents S and the other represents $CHR^3$. For example, Z may represent S and W may represent $CHR^3$. In compounds of formula I in which one of W and Z represents S and the other represents $CHR^3$, preferably $R^3$ represents —CN.

In embodiments of the invention, e.g. for compounds of formula IA, $R^3$ may represent $C_{1-6}$ alkyl, optionally substituted by one or more substituents selected from the list consisting of halogen atoms, —$OR^5$ groups and 5-membered heteroaryl groups. In other particular embodiments, W represents $CHR^3$, Z represents $CH_2$, and $R^3$ represents $C_{1-6}$ alkyl optionally substituted by one or more or more substituents selected from the list consisting of —OH and thiophenyl. In another particular embodiment, W represents $CHR^3$, Z represents $CH_2$, and $R^3$ represents a $C_{1-6}$ alkyl group which contains at least one —OH substituent (optionally in addition to one or more of the other substituents mentioned above). In preferred embodiments, W represents $CHR^3$, Z represents $CH_2$, and $R^3$ represents:

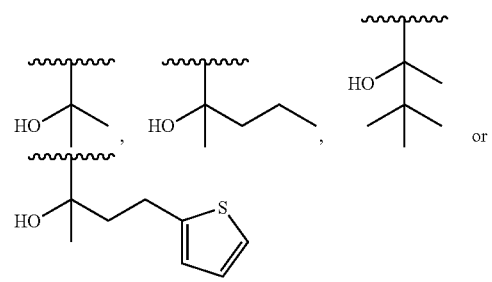

wherein ⌇⌇⌇ represents the point of attachment of $R^3$ to the rest of the compound of formula I.

Preferred groups which may be represented by $R^2$ include —$OR^4$ and —$OC(O)R^4$. In particular embodiments, $R^2$ represents a methoxy, ethoxy, propoxy or butoxy group. In the most preferred embodiments, $R^2$ represents a methoxy group.

A particular compound of formula I that may be mentioned in this respect is buprenorphine:

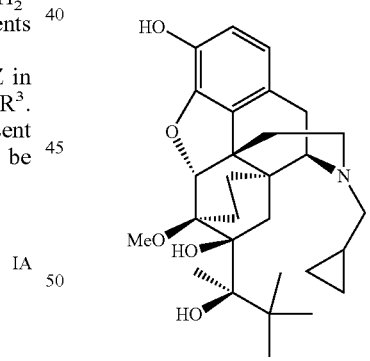

which may be prepared by demethylation of an appropriate compound of formula II (3-O-methyl buprenorphine) according to the processes described herein.

The processes of the invention involve contacting a compound of formula II, or a salt thereof, with an alkali metal borohydride and an additional alkali metal salt. The requisite reactants may be brought together in any order.

For the avoidance of doubt, the alkali metal of the alkali metal borohydride may be different from the alkali metal of the additional alkali metal salt used in the processes described herein. However, in particular embodiments of the invention, the alkali metal borohydride and the additional alkali metal salt each comprise the same alkali metal.

The processes of the invention are performed in the presence of an alkali metal borohydride. Suitable alkali metal borohydrides include compounds of formula III,

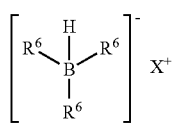

III wherein each $R^6$ independently represents $C_{1-12}$ alkyl; and $X^+$ represents an alkali metal cation.

Particular examples of alkali metal borohydrides of formula III include those in which $R^6$ represents methyl, ethyl, propyl, butyl (e.g. sec-butyl), pentyl or siamyl (i.e. 1,2-dimethylpropyl). In particular embodiments, $R^6$ represents sec-butyl or siamyl. In preferred embodiments, the alkali metal borohydride is an alkali metal tri-sec-butylborohydride or an alkali metal trisiamylborohydride.

Other particular examples of alkali metal borohydrides of formula III include those in which $X^+$ represents a lithium, sodium, potassium, rubidium or caesium cation. In preferred embodiments, $X^+$ represents a lithium cation.

Particular alkali metal borohydrides of formula III that may be mentioned include sodium triethylborohydride, lithium triethylborohydride (Super-Hydride®), potassium triethylborohydride, sodium tri-sec-butylborohydride (N-Selectride®), lithium tri-sec-butylborohydride (L-Selectride®), potassium tri-sec-butylborohydride (K-Selectride®), lithium trisiamylborohydride (LS-Selectride®) and potassium trisiamylborohydride (KS-Selectride®).

In more particular embodiments, the alkali metal borohydride of formula III is selected from the group consisting of sodium tri-sec-butylborohydride, lithium tri-sec-butylborohydride and potassium tri-sec-butylborohydride. In preferred embodiments, the alkali metal borohydride is lithium tri-sec-butylborohydride.

For the avoidance of doubt, mixtures of two or more of said alkali metal borohydrides may be used in the processes described herein. However, in particular embodiments of the invention, only one alkali metal borohydride is provided.

The amount of the alkali metal borohydride should be sufficient to enable the reaction to proceed (e.g. at a predetermined rate, in order to maximise yield, minimise reaction time, etc.). For example, the amount of alkali metal borohydride that is present in the reaction is at least about 1 (e.g. at least about 2) equivalent (i.e. molar equivalent) relative to the compound of formula II. In particular embodiments, the amount of alkali metal borohydride present is from about 1 to about 10 equivalents (e.g. from 2 to 9 equivalents) relative to the compound of formula II. In preferred embodiments, the amount of alkali metal borohydride present is from about 2 to about 5 (e.g. from about 2 to about 3) equivalents relative to the compound of formula II.

It is stated herein that the process of the invention is also performed in the presence of an additional alkali metal salt. By combining an additional alkali metal salt with the alkali metal borohydride, it has been found that the level of conversion is increased, the reaction time is shortened, and fewer equivalents of the alkali metal borohydride are needed, as compared to reactions in the absence of an additional alkali metal salt. Common examples of alkali metal salts include alkali metal acetates, carbonates, citrates, cyanides, halides, hydroxides, iodates, nitrates, phosphates, sulfides, sulfates and tetrafluoroborates. In particular embodiments, the additional alkali metal salt is an alkali metal halide.

Particular alkali metal salts that may be mentioned include lithium fluoride, lithium chloride, lithium bromide, lithium iodide, sodium fluoride, sodium chloride, sodium bromide, sodium iodide, potassium fluoride, potassium chloride, potassium bromide, potassium iodide, rubidium fluoride, rubidium chloride, rubidium bromide, rubidium iodide, caesium fluoride, caesium chloride, caesium bromide and caesium iodide. In preferred embodiments, the additional alkali metal salt is a lithium halide, such as lithium bromide.

The amount of the additional alkali metal salt should be sufficient to enable the reaction to proceed (e.g. at a predetermined rate, in order to maximise yield, minimise reaction time, etc.). For example, the additional alkali metal salt that is used in the reaction contains at least about 1 equivalent (i.e. molar equivalent) of alkali metal cations (e.g. $Li^+$) relative to the compound of formula II. In particular embodiments, the additional alkali metal salt contains from about 1 to about 6 equivalents (e.g. from 2 to 5 equivalents) of alkali metal cations relative to the compound of formula II. In preferred embodiments, the additional alkali metal salt contains from about 1.5 to about 3 equivalents of alkali metal cations relative to the compound of formula II.

For the avoidance of doubt, mixtures of two or more of said additional alkali metal salts may be used in the processes described herein. However, in particular embodiments of the invention, only one additional alkali metal salt is present.

For the avoidance of doubt, the additional alkali metal salt may be added to the reaction at any time. In particular embodiments, the compound of formula II is brought into contact with the additional alkali metal salt before the compound of formula II is brought into contact with the alkali metal borohydride.

The process of the invention is typically conducted in the presence of a solvent, for example a solvent (or solvent mixture) that is known to one skilled in the art as being suitable for use with a borohydride reducing agent. Common solvents that may be suitable for use in processes of the invention include pentane, hexane, heptane, octane, benzene, toluene, diethyl ether, diisopropyl ether, tert-butyl methyl ether, tert-butyl ethyl ether, dimethoxyethane, tetrahydrofuran, 2-methyltetrahydrofuran, 1,4-dioxane, dichloromethane, dichloroethane, chloroform and carbon tetrachloride. In preferred embodiments, the solvent is an ether, such as tetrahydrofuran or, particularly, 2-methyltetrahydrofuran.

Processes of the invention in which the solvent system consists essentially of 2-methyltetrahydrofuran are particularly advantageous. By "consisting essentially of" we mean that the solvent mixture comprises at least 90% (by weight of the solvents) 2-methyltetrahydrofuran, preferably at least 95% by weight of the solvents. This choice of solvent system allows the reaction to be run at a relatively high temperature (e.g. from 90 to 100° C., well above the boiling point of 2-methyltetrahydrofuran) which in turn allows the reaction to be completed with a satisfactory yield in a much shorter time (e.g. approximately 2 hours, as compared with approximately 24 hours when the solvent system is predominantly tetrahydrofuran).

Solvent systems which consist essentially of 2-methyltetrahydrofuran are also useful solvents for reactions in which buprenorphine is produced by reaction of 3-O-methyl-buprenorphine with an alkali metal borohydride irrespective of whether an additional alkali metal salt is present. Thus, in a second aspect of the invention, there is provided a process for the preparation of buprenorphine, or a pharmaceutically acceptable salt thereof, wherein the process comprises contacting 3-O-methyl-buprenorphine with an alkali metal borohydride in a solvent system comprising 2-methyltetrahydrofuran. The features described herein in respect of preferred embodiments of the first and third aspect also apply in respect of this second aspect.

The process of the invention may be performed at room temperature or preferably at elevated temperature. For example, the process of the invention may be performed at temperatures greater than about 30° C., for instance greater than about 50° C., greater than about 70° C., greater than about 90° C., or at reflux. The reaction may be performed at a temperature of up to about 200° C. The upper temperature limit for the process of the invention is generally dependent upon the temperature at which decomposition of the compound of formula I or II becomes significant. Therefore, in particular embodiments, the process of the invention may be performed at a temperature of up to about 150° C. (e.g. from about 50° C. to about 140° C., 60° C. to about 130° C., 70° C. to about 120° C., 80° C. to about 110° C., such as about 90° C. to about 100° C.). Advantageously, the process of the invention may be conducted at relatively low temperatures (i.e. at or below 150° C.) to thereby avoid the need for specialised heating equipment during manufacture while maintaining a good yield and efficiency.

In a further embodiment of the invention, the compound of formula I may be further purified by crystallisation from a suitable solvent. For instance, the compound of formula I may be dissolved to obtain a solution of that compound in a solvent (in particular, an organic solvent, e.g. an alcohol). The compound of formula I (in solvent) may be diluted with a different solvent in order to promote the crystallisation of the compound of formula I. In particular embodiments, that different solvent is water.

Preferences and options for a given aspect, feature or parameter of the invention should, unless the context indicates otherwise, be regarded as having been disclosed in combination with any and all preferences and options for all other aspects, features and parameters of the invention. For example, any preferred definitions and/or quantities for the alkali metal borohydride may be combined with any preferred definitions and/or quantities for the additional alkali metal salt.

Therefore, in a further embodiment of the invention, the process is one which comprises adding an alkali metal borohydride to a mixture comprising:

(i) a compound of formula II, or a salt thereof; and (ii) an additional alkali metal salt.

In a yet further embodiment of the invention, the process is one in which the compound of formula I is buprenorphine, and the process comprises contacting 3-O-methyl-buprenorphine or a salt thereof with:

(i) an alkali metal borohydride selected from the group consisting of lithium tri-sec-butylborohydride, sodium tri-sec-butylborohydride, potassium tri-sec-butylborohydride, and mixtures thereof; and (ii) an additional alkali metal halide.

In this embodiment, the amount of alkali metal borohydride may be from about 2 to about 5 equivalents relative to the compound of formula II, and/or the amount of additional alkali metal halide present may be from about 1.5 to about 3 equivalents relative to the compound of formula II.

In particular embodiments of the invention, the process further comprises adding an oxidant after the compound of formula I has been formed. The term "oxidant", when used herein, refers to a substance that has the ability to oxidise other substances. Suitable oxidants may include amine N-oxides, bleach, inorganic perborates, inorganic peroxides, metal oxides, organic periodinanes, organic peroxides, organic peroxy acids, Oxone® and ozone.

In particular embodiments, the oxidant is an amine N-oxide. Specific amine N-oxides that may be mentioned in this respect include trialkylamine N-oxides such as triethylamine N-oxide and trimethylamine N-oxide, as well as cyclic amine N-oxides such as N-methylmorpholine N-oxide, pyridine N-oxide and mixtures thereof. Without wishing to be bound by theory, it is believed that, for use in the processes of the invention, the requisite nitrogen atom in the amine N-oxide should ideally be $sp^3$ hybridized. Thus, in particular embodiments, the amine N-oxide is selected from the list consisting of trimethylamine N-oxide and N-methylmorpholine N-oxide. In preferred embodiments, the amine N-oxide is trimethylamine N-oxide.

The use of an oxidant as described herein is particularly useful in reactions involving buprenorphine and borohydride reagents, regardless of whether an additional alkali metal salt is present.

Once the formation of buprenorphine is nearing completion, as may be determined using an appropriate analytical technique (e.g. chromatography), unreacted borohydride reagent may be quenched. Suitable quenching reagents include alcohols, such as primary alcohols (e.g. methanol and/or ethanol), secondary alcohols (e.g. isopropyl alcohol) and tertiary alcohols (e.g. tert-butanol). Quenching a borohydride reagent with an alcohol, such as methanol, is known to produce the corresponding borane. The term "quench", when used herein, refers to chemical manipulations that may be required to stop a particular chemical reaction. This can be achieved, for example, by adding another reagent (e.g. methanol) to a reaction mixture. A quench is often performed to prevent the formation of undesirable side products, which may result from the over-reaction of the starting reagents with a product of the reaction.

It has been found that, when an oxidant is used in these processes, it is effective at rapidly oxidising the borane produced by the alcohol quench, either partially or completely, to the corresponding borate ester. The conversion of boranes to borate esters greatly reduces the formation of undesirable by-products of the opioid. The cyclopropyl methyl moiety of buprenorphine has been found to be vulnerable to reaction with boranes produced by the alcohol quench, leading to the formation of by-products (such as norbuprenorphine and N-butyl-buprenorphine) in the work up. Therefore, the use of the oxidant in such reactions is particularly advantageous. Thus, in a third aspect of the present invention, there is provided a process for preparing buprenorphine, or a pharmaceutically acceptable salt thereof, which process comprises the steps of:

(i) contacting 3-O-methyl-buprenorphine with an alkali metal borohydride; and (ii) adding an oxidant to the mixture obtained from step (i).

In this process, the mixture obtained in step (i) is typically quenched, e.g. by adding an alcohol. It is also preferred that no water is introduced into the reaction mixture containing the 3-O-methyl-buprenorphine and the alkali metal borohydride (i.e. no aqueous quench is performed) prior to the introduction of the oxidant. This helps to reduce the formation of by-products (such as nor-buprenorphine in the case of reactions involving 3-O-methyl-buprenorphine). The oxidant may be introduced in any form, including in the form of an aqueous solution, though the oxidant is preferably provided in a non-aqueous form.

The features described herein in respect of the first and second aspects of the invention also apply in respect of this third aspect.

The amount of the oxidant added should be sufficient to rapidly and efficiently oxidise the borane produced by the alcohol quench, that is, to stop further reaction between the buprenorphine and the borane. In particular embodiments of the invention, the amount of oxidant added is at least about 1 equivalent (i.e. molar equivalent) and preferably at least about 3 equivalents relative to the total amount of alkali metal borohydride added to the reaction mixture. It is preferred that the amount of oxidant that is added is calculated based on the amount of alkali metal borohydride initially added, rather than the amount of alkali metal borohydride remaining at the time of quenching. For example, if a total of about 1 mole of alkali metal borohydride is used in the process of the invention, then at least about 1 mole of oxidant should be added at the quenching stage. In particular embodiments, the amount of oxidant added is from about 1 to about 10 equivalents relative to the total amount of alkali metal borohydride added to the reaction mixture. In preferred embodiments, the amount of oxidant added is from about 3 to about 7 equivalents relative to the alkali metal borohydride.

The oxidant is typically mixed with a solvent before being added to the reaction mixture. Solvents that may be suitable include water, methanol, ethanol, isopropanol and n-butanol. In preferred embodiments, the solvent is methanol.

Once the oxidant has been added, the process may be performed at room temperature or at elevated temperature. In particular embodiments of the invention, the reaction with the oxidant is performed at elevated temperature. For example, the process may be performed at temperatures greater than about 30° C., for instance greater than about 50° C., greater than about 70° C. or greater than about 90° C. The upper temperature limit for the process is generally dependent upon the temperature at which decomposition of the compound of formula I becomes significant. Therefore, in particular embodiments, the process of the invention may be performed at a temperature of up to about 150° C. (e.g. from about 50° C. to about 140° C., 60° C. to about 130° C., 70° C. to about 120° C., 80° C. to about 110° C., such as about 90° C. to about 100° C.).

The use of an amine N-oxide as the oxidant typically leads to the formation of the corresponding amine as a degradation-product. Removal of amine degradation-products, e.g. trimethylamine or N-methyl morpholine, was found to advantageously result in consistently high yields of buprenorphine product, with low impurity levels. Removal of undesirable amine, e.g. triethylamine or N-methyl morpholine, from the reaction mixture may be achieved by conducting a nitrogen sweep of the reaction vessel headspace into a scrubber containing aqueous hydrochloric acid.

In a further embodiment, the compound of formula I, which is produced by a process involving the addition of an oxidant, may be further purified by crystallisation from a suitable solvent. For instance, the compound of formula I may be dissolved to obtain a solution of that compound in a solvent (in particular, an organic solvent, e.g. an alcohol). The compound of formula I (in solvent) may be diluted with a different solvent in order to promote the crystallisation of the compound of formula I. In particular embodiments, that different solvent is water.

Compounds of formula II may be known or easily derived/synthesised from known compounds using standard steps or transformations known to those skilled in the art.

However, in a further embodiment of the invention, the compound of formula II is first formed by a process comprising reacting a compound of formula IV,

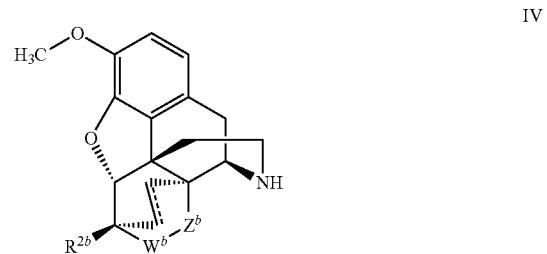

or a salt thereof, wherein $R^{2b}$, $W^b$ and $Z^b$ are defined according to $R^2$, W and Z, respectively, with a compound of formula V,

wherein $R^7$ represents $C_{1-12}$ alkyl, $C_{2-12}$ alkenyl, $C_{2-12}$ alkynyl or $C_{3-12}$ cycloalkyl, which groups are optionally substituted by one or more substituents selected from the group consisting of halogen atoms, phenyl groups and $C_{3-12}$ cycloalkyl groups; and Y represents a suitable leaving group.

The term "leaving group", when used herein, refers to a molecular fragment that departs a parent molecule as a result of heterolytic bond cleavage. Leaving groups may be anions or neutral molecular species. Common anionic leaving groups includes halides such as chloro, bromo and iodo, and sulfonate esters such as mesylate and tosylate. Common neutral leaving groups include water, ammonia and methanol (thus in each case Y represents —OH, —NH$_2$ or —OMe, respectively).

Particular $R^7$ groups that may be mentioned include $C_{1-6}$ alkyl, $C_{2-6}$ alkenyl, $C_{2-6}$ alkynyl and $C_{3-6}$ cycloalkyl, each of which is optionally substituted by one or more substituents selected from the group consisting of halogen atoms, phenyl groups and $C_{3-6}$ cycloalkyl groups. In preferred embodiments, $R^7$ represents methyl, ethyl, propyl, butyl, benzyl or —CH$_2$-cyclopropyl.

In an embodiment of the invention in which the compound of formula II is 3-O-methyl-buprenorphine, the process further comprises the preceding step of converting 3-O-methyl-norbuprenorphine to 3-O-methyl-buprenorphine. This conversion may be achieved, for example, by any of the methods described herein.

In particular embodiments of the invention, Y in the compound of formula V represents a halide or a sulfonate ester group. In preferred embodiments, Y represents chloro, bromo, iodo, mesylate or tosylate.

In embodiments of the invention which involve the reaction between a compound of formula IV and a compound of formula V, the reaction between the compounds of formulae IV and V may be performed in the presence of an inorganic base. Inorganic bases that may be mentioned include lithium hydroxide, sodium hydroxide, potassium hydroxide, caesium hydroxide, lithium carbonate, potassium carbonate, caesium carbonate, magnesium carbonate, calcium carbonate, barium carbonate, potassium phosphate monobasic, potassium phosphate dibasic and potassium phosphate tribasic. In preferred embodiments, the inorganic base is potassium phosphate tribasic.

The amount of the compound of formula V should be sufficient to enable the reaction with the compound of formula IV to proceed fully. For example, the amount of compound of formula V that is used in the reaction is at least about 1 equivalent (i.e. molar equivalent) relative to the compound of formula IV. In particular embodiments, the amount of compound of formula V used is from about 1 to about 5 equivalents (e.g. from 1.5 to 3 equivalents) relative to the compound of formula IV.

In embodiments of the invention which involve the reaction of a compound of formula IV with a compound of formula V, the reaction between these compounds is typically conducted in the presence of a solvent. Solvents that may be suitable for use in such reactions include pentane, hexane, heptane, octane, benzene, toluene, diethyl ether, diisopropyl ether, tert-butyl methyl ether, tert-butyl ethyl ether, dimethoxyethane, tetrahydrofuran, 2-methyltetrahydrofuran, 1,4-dioxane, ethyl acetate, acetonitrile, dimethylformamide, dimethyl sulfoxide, dichloromethane, dichloroethane, chloroform and carbon tetrachloride. In preferred embodiments, the solvent is acetonitrile.

The reaction between a compound of formula IV and a compound of formula V may be performed at room temperature or at elevated temperature. For example, the reaction may be performed at temperatures greater than about 30° C., for instance greater than about 40° C. or greater than about 50° C. Preferably the process is performed at a temperature of about 50° C.

In a further embodiment of the invention, the process is one which comprises contacting a compound of formula V, as defined herein, or a salt thereof, with a mixture comprising:
  (i) a compound of formula IV; and
  (ii) an inorganic base.

In another embodiment of the present invention, particularly one in which the compound of formula II is 3-O-methyl-buprenorphine, the compound of formula II may be formed from 3-O-methyl-norbuprenorphine.

Thus, there is provided a process for forming buprenorphine, wherein the process comprises:
  (i) converting 3-O-methyl-norbuprenorphine to 3-O-methyl-buprenorphine; and
  (ii) converting said 3-O-methyl-buprenorphine to buprenorphine according to a process as described herein.

3-O-methyl-norbuprenorphine may be synthesised by any method known to those skilled in the art; for example, the method described in U.S. Pat. No. 8,232,397.

Both the free-base and salts of a compound of formula IV may be used in a process to produce a compound of formula II. It may be possible to form a salt of a compound of formula IV from the corresponding free-base using any process known to those skilled in the art. For example, such a salt may be formed by bringing into association the compound of formula IV with an acid (e.g. an organic acid) under appropriate reaction conditions, for example in the presence of a solvent (e.g. water, an alcohol (such as methanol or ethanol), acetonitrile, diethyl ether, 1,4-dioxane, or a mixture thereof), for example at or above room temperature (e.g. from room temperature to 105° C.), followed by removal of the solvent to afford the isolated salt (or solvate). The salt obtained in this method, or any other, may also be converted into a different salt by any process known to a person skilled in the art, for example using a suitable ion exchange resin.

Particular salts that may be mentioned include carboxylate (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, a-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxybenzoate, salicylate, nicotinate, isonicotinate, cinnamate, oxalate, malonate, succinate, suberate, sebacate, fumarate, malate, maleate, hydroxymaleate, hippurate, phthalate or terephthalate), halide (e.g. chloride, bromide or iodide), sulphonate (e.g. benzenesulphonate, methyl-, bromo- or chloro-benzenesulphonate, xylenesulphonate, methanesulphonate, ethanesulphonate, propanesulphonate, hydroxyethane-sulphonate, 1- or 2-naphthalene-sulphonate or 1,5-naphthalene-disulphonate), sulphate, pyrosulphate, bisulphate, sulphite, bisulphite, phosphate, monohydrogenphosphate, dihydrogenphosphate, metaphosphate, pyrophosphate and nitrate salts, and the like.

More particular salts of a compound of formula IV (e.g. 3-O-methyl-norbuprenorphine) that may be mentioned include the trifluoroacetate salt. Thus, in a particular embodiment, the compound of formula IV (e.g. 3-O-methyl-norbuprenorphine) is the trifluoroacetate salt.

Compounds of formula I in which one of W and Z represents S and the other represents —CH(CN)— effectively represent a protected diene system in which the diene is protected in the form of a [4+2] cycloaddition adduct with a thioaldehyde. Such compounds may be used to prepare compounds of formula VI

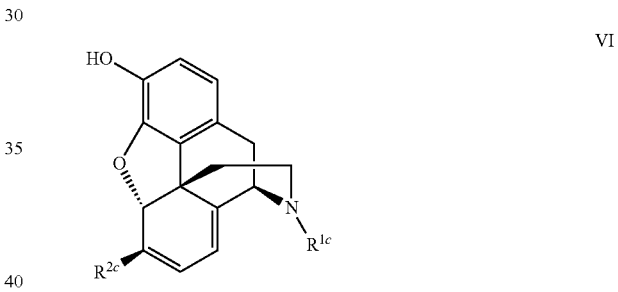

VI in which $R^{1c}$ and $R^{2c}$ are as defined in respect of $R^1$ and $R^2$, respectively. This process may be achieved by way of a retro-Diels-Alder reaction, e.g. under conditions that would be known to those skilled in the art. Suitable conditions include those disclosed in Hudlicky, Can. J. Chem. 93, 2015, 492-501 (Scheme 12). Thus, this process may be useful for forming oripavine and structurally related compounds.

In a further aspect of the invention, there is provided a process for preparing a compound of formula VI (e.g. oripavine) as defined above, which process comprises the steps of:
  (i) preparing a compound of formula I (e.g. one in which one of W and Z represents S and the other represents —CH(CN)—) by demethylating a corresponding compound of formula II according to any one of the processes disclosed herein;
  (ii) optionally isolating and/or purifying the compound of formula I obtained from that process; and
  (iii) reacting the compound of formula I (e.g. one in which one of W and Z represents S and the other represents —CH(CN)—) under suitable conditions to perform a retro-Diels-Alder reaction to form a compound of formula VI.

In a further embodiment of the invention there is provided a process for preparing a pharmaceutically acceptable salt of a compound of formula I, as defined above, which process comprises the steps of:

(i) preparing a compound of formula I by demethylating a compound of formula II, as defined above, according to any one of the processes disclosed herein;

(ii) optionally isolating and/or purifying the compound of formula I obtained from that process; and (iii) bringing into association the compound of formula I so formed with an acid (e.g. an organic acid) under reaction conditions known to those skilled in the art, for example in the presence of a solvent (e.g. water, an alcohol (such as methanol or ethanol), acetonitrile, diethyl ether, 1,4-dioxane, or a mixture thereof), for example at or above room temperature (e.g. from room temperature to 105° C.), followed by removal of the solvent to afford the isolated salt (or solvate). The salt obtained in this method, or any other, may also be converted into a different salt by any process known to a person skilled in the art.

In a further embodiment of the invention there is provided a process for preparing a pharmaceutical formulation comprising a compound of formula I, or a pharmaceutically acceptable salt thereof, as defined above, which process comprises the steps of:

(i) preparing a compound of formula I by demethylating a compound of formula II, as defined above, according to any one of the processes disclosed herein;

(ii) optionally isolating and/or purifying the compound of formula I (or pharmaceutically acceptable salt thereof) obtained from step (i); and (iii) bringing into association the compound of formula I so formed (or pharmaceutically acceptable salt thereof) with one or more pharmaceutically acceptable excipients, adjuvants, diluents or carriers.

According to a further aspect of the invention there is provided a pharmaceutical composition comprising a compound of formula I (e.g. buprenorphine), or a pharmaceutically salt thereof, obtained by any one of the processes disclosed herein, and one or more pharmaceutically acceptable excipients, diluents or carriers.

Products of the process of the invention may be useful in further processes for the preparation of derivatives of a compound of formula I (e.g. acetorphine, and other acyl derivatives of the free hydroxyl group), and pharmaceutically acceptable salts thereof, which process comprises the steps of:

(i) preparing a compound of formula I by demethylating a compound of formula II, as defined above, according to any one of the processes disclosed herein;

(ii) optionally isolating and/or purifying the compound of formula I obtained from that process; and (iii) bringing into association the compound of formula I so formed with a suitable chemical reagent (e.g. an organic acid chloride) under reaction conditions known to those skilled in the art, for example in the presence of a solvent (e.g. acetonitrile, diethyl ether, 1,4-dioxane, dimethyl formamide, dichloromethane or a mixture thereof), for example at or above room temperature (e.g. from room temperature to 105° C.), followed by appropriate isolation techniques known to a person skilled in the art. A derivative obtained in this method, or any other, may also be converted into a different derivative by any process known to a person skilled in the art.

By way of an example, acetorphine may be made by a process in which the compound of formula I is reacted with an acetyl donor (such as acetoyl chloride or acetic acid anhydride) under appropriate conditions as described above.

The compounds of formula I obtained by the processes of the first to third aspects of the invention may be separated and/or isolated by standard techniques used in the art, for example by chromatography, crystallisation, evaporation of solvents and/or by filtration.

Purification may be performed in order to reduce the levels of certain impurities present in the product of the O-demethylation step. Such impurities include derivatives of compounds of formula I wherein $R^1$ is hydrogen (e.g. norbuprenorphine). The amount of such impurities present in a given sample may be determined by any conventional method known to the person skilled in the art, such as liquid chromatography-mass spectrometry (LCMS) and the like, or any method disclosed herein.

The processes described herein may be operated as a batch process or operated as a continuous process and may be conducted on any scale.

In general, the processes described herein may have the advantage that they achieve higher levels of conversion and/or fewer undesired by-products (resultant of undesired side reactions) may be produced, for example, by-products that may require difficult and/or expensive purification steps. In particular, it is desirable to reduce the amount of certain impurities that may be formed, particularly compounds of formula I wherein $R^1$ is hydrogen or n-butyl, as these impurities, along with the starting compound of formula II, may be particularly difficult to separate from the desired product. The processes may also be more economical or efficient than those described in the prior art.

Processes described herein may also have the advantage that the compounds of formula I may be produced in a manner that requires less time, utilises fewer reagents and/or solvents, and/or requires fewer reaction steps (e.g. distinct/separate reaction steps) at a lower cost and/or with less usage and/or wastage of materials (including reagents and solvents) compared to processes disclosed in the prior art.

The processes described herein may also reduce the need to work with reagents or processing conditions that may be toxic or otherwise hazardous to work with, e.g. corrosive reagents and/or high temperatures (e.g. as are involved when demethylation is achieved using KOH). Furthermore, the processes described herein may also achieve high levels of conversion whilst avoiding the need for particularly high temperatures (e.g. above 150° C.) that require specialised equipment.

The following examples are merely illustrative examples of the processes of the invention described herein.

All equipment, reagents and solvents used were standard laboratory equipment, e.g. glassware, heating apparatus and HPLC apparatus.

EXAMPLES

Example 1

Methylcyclopropylation of
3-O-methyl-norbuprenorphine

A mixture of 3-O-methyl-norbuprenorphine TFA salt (50.0 g, 78 mmol, assay: 85%) and $K_3PO_4$ (66.6 g, 314 mmol) in MeCN (200 mL) was treated with (bromomethyl)cyclopropane (11.4 mL, 118 mmol). The mixture was stirred and heated to 50±5° C. for at least 24 hr. The reaction was considered complete when the level of 3-O-methyl-norbuprenorphine present was found to be not more than 1% using UPLC/MS.

The mixture was then cooled to 40±5° C. and treated with MTBE (250.0 mL) and water (250 mL), and stirred for 10 min. The resultant phases were allowed to separate and the aqueous phase was discarded. The mixture was treated again with water (250 mL), and stirred for a further 10 min. The phases were allowed to separate and the aqueous phase was discarded. To the organic phase was added 2-MeTHF (250 mL) and approximately 6 volumes were distilled off under atmospheric pressure. The mixture was treated again with 2-MeTHF (250 mL) and approximately 6 volumes (i.e. 6 mL of solvent per gram of starting opioid) were again distilled off under atmospheric pressure. The resultant mixture was used in Example 2 without further purification.

Example 2

Demethylation of 3-O-methyl-buprenorphine

In a separate vessel, LiBr (11.93 g, 137 mmol) was treated with 2-MeTHF (250 mL), and the mixture was stirred at room temperature until the LiBr had dissolved.

The product mixture of Example 1 was added to the LiBr mixture and approximately 6 volumes were distilled off under atmospheric pressure. The mixture was treated with 2-MeTHF (250 mL) and approximately 6 volumes were distilled off under atmospheric pressure. The mixture was further treated with 2-MeTHF (250 mL) and approximately 6 volumes were distilled off under atmospheric pressure.

The mixture was cooled to 50±5° C. and treated with lithium tri-sec-butylborohydride (L-Selectride® 1 M in THF, 220.3 mL, 220 mmol). The mixture was heated under reflux and distilled under atmospheric pressure until the reaction temperature reached 100±5° C. The mixture was heated at 100±5° C. for at least 1 hr. The reaction was considered complete when the 3-O-methyl-buprenorphine level was found to be not more than 0.1% using UPLC/MS. The mixture was then cooled to 60±5° C.

Example 3

Isolation of Buprenorphine

In a separate vessel, TMO dihydrate (80.58 g, 725 mmol) was mixed with MeOH (150 mL). The mixture was stirred at room temperature until the TMO dihydrate had dissolved.

The TMO mixture was added slowly to the buprenorphine mixture of Example 2 and then heated under reflux for 8 hr. Approximately 3 volumes were distilled off under atmospheric pressure and the mixture was then cooled to 25±5° C.

The mixture was treated with water (250 mL) and stirred for at least 1 hr. The mixture was treated dropwise with AcOH (11.78 g) until it reached a pH of between 7 and 8 and stirred for at least 30 min. The resultant precipitate was collected by filtration, rinsed twice with water (2×50 mL) and dried in vacuo at 40±5° C. overnight to afford buprenorphine (34.4 g, 74 mmol, >99.5% purity) as an off-white solid.

Example 4

Methylcyclopropylation of
3-O-methyl-norbuprenorphine

A mixture of 3-O-methyl-norbuprenorphine TFA salt (20.0 g, 31 mmol, assay: 85%) and K₃PO₄ (26.7 g, 126 mmol) in MeCN (80 mL) was treated with (bromomethyl) cyclopropane (4.6 mL, 47 mmol). The mixture was stirred and heated to 50±5° C. for at least 24 hr. The reaction was considered complete when the level of 3-O-methyl-norbuprenorphine present was found to be not more than 0.2% using IPC.

The mixture was then cooled to 40±5° C. and treated with MTBE (100.0 mL) and water (100 mL), and stirred for 10 min. The resultant phases were allowed to separate and the aqueous phase was discarded. The mixture was treated again with water (100 mL), and stirred for a further 10 min. The phases were allowed to separate and the aqueous phase was discarded. To the organic phase was added 2-MeTHF (100 mL) and approximately 6.6 volumes were distilled off under atmospheric pressure. The mixture was treated again with 2-MeTHF (100 mL) and approximately 6.6 volumes were again distilled off under atmospheric pressure. The resultant mixture was used in Example 5 without further purification.

Example 5

Demethylation of 3-O-methyl-buprenorphine

In a separate vessel, LiBr (4.8 g, 137 mmol) was treated with 2-MeTHF (100 mL), and the mixture was stirred at room temperature until the LiBr had dissolved.

The product mixture of Example 4 was treated with the LiBr mixture and approximately 6.6 volumes were distilled off under atmospheric pressure. The mixture was treated with 2-MeTHF (100 mL) and approximately 6.6 volumes were distilled off under atmospheric pressure until the supernatant contained less than 440 ppm of water as determined by volumetric Karl-Fischer titration. The mixture was treated with 2-MeTHF (100 mL) and approximately 6.6 volumes were distilled off under atmospheric pressure.

The mixture was cooled to 50±5° C. and treated with lithium tri-sec-butylborohydride (L-Selectride® 1 M in THF, 88.1 mL, 88 mmol). The mixture was heated under reflux and approximately 6.6 volumes were distilled under atmospheric pressure until the reaction temperature reached 100±5° C. The mixture was heated at 100±5° C. for at least 1 hr. The reaction was considered complete when the 3-O-methyl-buprenorphine level was found to be not more than 0.1% using UPLC/MS. The mixture was then cooled to 60±5° C.

Example 6

Isolation of Buprenorphine

In a separate vessel, TMO dihydrate (32.32 g, 290 mmol) was mixed with MeOH (60 mL). The mixture was stirred at room temperature until the TMO dihydrate had dissolved.

The buprenorphine mixture of Example 5 was added slowly to the TMO mixture at a rate to maintain reflux. The reaction mixture was held at reflux for 8 hr and then cooled to 25±5° C.

The mixture was treated slowly with 10% aqueous AcOH (103.7 mL) until it reached a pH of between 5.2 and 5.4. The phases were allowed to separate and the aqueous phase was discarded. The mixture was treated with water (45.4 mL) and stirred for at least 1 hr. The phases were allowed to separate, the aqueous phase was discarded and approximately 6 volumes were distilled under atmospheric pressure. The mixture was treated with MeCN (75.6 mL) and approximately 5 volumes were distilled under atmospheric pressure. The mixture was treated with water (45.4 mL), approximately 5 volumes were distilled under atmospheric pressure and cooled to 0±5° C. The resultant precipitate was collected by filtration, rinsed with water (45.4 mL) and dried in vacuo at 40±5° C. overnight to afford buprenorphine (13.8 g, 29.5 mmol, >99.5% purity) as an off-white solid.

Example 7

Analysis of Critical Parameters for the Demethylation Reaction

The demethylation of 3-O-methyl-buprenorphine to buprenorphine was investigated using L-Selectride® (or Superhydride®), lithium bromide and 2-methyltetrahydrofuran. Except where specified, the methods used followed the method described in Example 5. See Experiment nos. 1 to 29 in Table 1 below.

Experiment nos. 11 to 17 included a prior step in which 3-O-methyl-norbuprenorphine was alkylated to form 3-O-methyl-buprenorphine using the conditions described in Example 4 (i.e. using approx. 4 equivalents $K_3PO_4$ and 1.5 equivalents cyclopropylmethylbromide relative to the 3-O-methyl-norbuprenorphine).

Results

Table 1 below shows the results obtained after a reaction time of 24 hrs using different amounts alkali metal borohydride and lithium bromide, and at different reaction temperatures. The L-Selectride®, Superhydride® and lithium bromide quantities are expressed as molar equivalents relative to the amount of the starting buprenorphine derivative used (e.g. the 3-O-methyl-norbuprenorphine or 3-O-methyl-buprenorphine, as appropriate).

TABLE 1

Demethylation of 3-O-methyl-buprenorphine

| Experiment no. | Scale (g) | Temp (° C.) | AMBH | AMBH (eq) | LiBr (eq) | 3OMB area % | Bup area % |
|---|---|---|---|---|---|---|---|
| 1 (part 1) | 10 | 100 | LS | 2.8 | 1.75 | 0 | 99.6 |
| 2 (part 1) | 5 | 87 | LS | 2.25 | 3 | 0.27 | 99.6 |
| 3 (part 1) | 10 | 100 | LS | 2.80 | 2.00 | 0.03 | 99.97 |
| 4 | 5 | 100 | SH | 3.6 | 2.75 | 80 | 20 |
| 5 (part 1) | 10 | 100 | LS | 3 | 2 | ND | ND |
| 6 | 5 | 80 | LS | 3 | 0 | 30 | 70 |
| 7 (part 1) | 5 | 100 | LS | 2.6 | 3.5 | 1 | 99 |
| 8 | 5 | 100 | LS | 2 | 1.75 | 0 | 76 |
| 9 (part 1) | 5 | 100 | LS | 2.6 | 3 | 0.02 | 99.8 |
| 10 (part 1) | 5 | 100 | LS | 2.8 | 2 | 0 | 100 |
| 11 | 20 | 100 | LS | 3.05 | 1.75 | 0.9 | 99.1 |
| 12a | 5 | 100 | TSBB | 2.8 | 1.75 | 84.59 | 12.6 (nor 3OMnB) |
| 12b | 5 | 100 | LS[a] | 2.8 | 1.75 | 64.18 | 33.07 |
| 13 (part 1) | 50 | 100 | LS | 2.8 | 2 | ND | 99.7 |
| 14 (part 1) | 20 | 100 | LS | 2.8 | 2 | ND | ND |
| 15 (part 1) | 20 | 100 | LS | 2.8 | 2 | 0.07 | ND |
| 16 (part 1) | 10 | 100 | LS | 2.8 | 2 | 0.06 | 99.6 |
| 17 (part 1) | 70 | 100 | LS | 2.8 | 2 | ND | 99.9 |
| 18 (part 1) | 20 | 100 | LS | 2.8 | 1.75 | 0.15 | 99.85 |
| 19 (part 1) | 20 | 100 | LS | 2.8 | 1.75 | 0.0 | 100.0 |
| 20 (part 1) | 20 | 100 | LS | 2.8 | 1.75 | 0.0 | 100.0 |
| 21 (part 1) | 20 | 100 | LS | 2.8 | 1.75 | 0.0 | 100.0 |
| 22 (part 1) | 20 | 100 | LS | 2.8 | 1.75 | 0.04 | 99.96 |
| 23 (part 1) | 20 | 100 | LS | 2.8 | 1.75 | 0.0 | 100.0 |
| 24 (part 1) | 20 | 100 | LS | 2.8 | 1.75 | ND | ND |
| 25 (part 1) | 20 | 100 | LS | 2.8 | 1.75 | 0.0 | 99.86 |
| 26 (part 1) | 20 | 100 | LS | 2.8 | 1.75 | 0.0 | 99.79 |
| 27 (part 1) | 20 | 100 | LS | 2.8 | 1.75 | 0.0 | 100.0 |
| 28 (part 1) | 71 | 100 | LS | 2.8 | 1.75 | 0.0 | 100.0 |
| 29 (part 1) | 1000 | 100 | LS | 2.8 | 1.75 | 0.03 | 99.89 |

[a]L-Selectride formed in-situ using the method described by P. Gartner et. al., ARKIVOC, 2001, 2, 9-20.
ND: not determined Example 8

Analysis of Critical Parameters for the Isolation of Buprenorphine

The isolation of buprenorphine was assessed using a mixture of buprenorphine as produced in Example 7, trimethylamine N-oxide as the oxidant, and a suitable solvent using the method described in Example 6.

Results

Table 2 below shows the results obtained after a reaction time of at least 8 hrs, unless states otherwise, using different amounts of trimethylamine N-oxide, with different solvents, different reaction temperatures, and with and without an active nitrogen sweep of the reaction headspace. The quantity of trimethylamine N-oxide is expressed as molar equivalents relative to the amount alkali metal borohydride used in Example 7.

TABLE 2

Isolation of buprenorphine

| Experiment no. | Scale (g) | Temp ° C. (time) | Oxidant (equiv) | Isolation Solvent | Bup area % | norBup area % | Isolated yield % |
|---|---|---|---|---|---|---|---|
| 1 (part 2) | 10 | 10-79 (2 h) | TMO (9.24) | MeOH | 99.62 | 0.19 | 91 |
| 2 (part 2) | 5 | 60 | TMO (9.24) | MeOH | 99.73 | 0.03 | 87 |
| 3 (part 2) | 10 | 60 | TMO (11.76) | MeOH | 99.8 | 0.05 | 86 |
| 5 (part 2) | 10 | 40 | TMO (6.6) | AcOH | 99.9 | ND | 86 |
| 7 (part 2) | 5 | 60 → reflux (2.5 h) | TMO (10.8) | MeOH | 99.22 | 0.11 | 80 |
| 9 (part 2) | 5 | 60-65 (18 h) | TMO (11) | MeOH | 99.6 | 0.11 | 94 |
| 10 (part 2) | 10 | 60 | — | $H_2O$ | 99.66 | 0.35 | 95 |
| 13 (part 2) | 50 | 60 | TMO (11.76) | MeOH | 99.8 | 0.05 | 94 |
| 14 (part 2) | 20 | 60 | TMO (11.76) | MeOH | 99.7 | 0.05 | 92 |
| 15 (part 2) | 20 | 60 | TMO (11.76) | MeOH | 99.8 | 0.06 | 87 |
| 16 (part 2) | 10 | 60 | TMO (11.76) | MeOH/ $H_2O$ | 99.6 | 0.06 | 98 |
| 17 (part 2) | 70 | 60 → reflux (4.5 h) | TMO (9.24) | MeOH | 99.9 | 0.1 | 85 |
| 18 (part 2)[b] | 20 | 60 → reflux (5 h) | TMO (9.24) | MeOH | 98.9 | 1.13 | 86 |
| 19 (part 2)[b] | 20 | 60-78 (7 h) | TMO (9.24) | IPA | >99.9 | 0.0 | not isolated |
| 20 (part 2)[b] | 20 | 60 → reflux (25 h) | TMO (9.24) | MeOH | 99.73 | 0.06 | >100 |
| 21 (part 2)[b] | 20 | 60 → reflux (21.5 h) | TMO (9.24) | MeOH | 100 | 0.0 | 70 |
| 22 (part 2)[b] | 20 | 60 → reflux (22.5 h) | TMO (9.24) | MeOH | 99 | 0.0 | 64 |
| 23 (part 2)[b,c] | 20 | 60 → reflux (22 h) | TMO (9.24) | MeOH | 99.7 | 0.0 | 80 |
| 24 (part 2)[b,c] | 20 | 60 → reflux (24.5 h) | TMO (9.24) | MeOH | 99.82 | 0.03 | 83 |

TABLE 2-continued

Isolation of buprenorphine

| Experiment no. | Scale (g) | Temp °C. (time) | Oxidant (equiv) | Isolation Solvent | Bup area % | norBup area % | Isolated yield % |
|---|---|---|---|---|---|---|---|
| 25 (part 2) [b,c] | 20 | 60 → reflux (21 h) | TMO (9.24) | MeOH | 99.98 | 0.02 | 80 |
| 26 (part 2) [b,c] | 20 | 60 → reflux (28 h) | TMO (9.24) | MeOH | >99.9 | 0.00 | 86 |
| 27 (part 2) [b,c] | 20 | 60 → reflux (19 h) | TMO (9.24) | MeOH | >99.9 | 0.00 | 92 |
| 28 (part 2) [b,c] | 72 | 60 → reflux (72 h) | TMO (9.24) | MeOH | >99.9 | 0.00 | 93 |
| 29 (part 2) [b,c] | 1000 | 60 → reflux (43 h) | TMO (9.24) | MeOH | 99.96 | 0.00 | 91 |

[b] The reaction was performed by addition of the buprenorphine mixture to the trimethylamine N-oxide mixture, i.e. via inverse addition.
[c] A nitrogen sweep of the reaction vessel headspace into a HCl (6M aq.) scrubber was used to remove trimethylamine from the reaction mixture.

It was found that the addition of at least about 3 molar equivalents of oxidant relative to the borohydride (which corresponds approximately to about 8 to 10 molar equivalents relative to the compound of formula II) optimised the suppression of impurities and provided buprenorphine at high levels of purity and in high yields. In particular, it was found that by using trimethylamine N-oxide in MeOH, the excess L-Selectride®, and corresponding by-products derived from L-Selectride®, could be quenched. By quenching the boron containing by-products with trimethylamine N-oxide, the suppression of impurities, namely norbuprenorphine, was achieved.

In addition, it was found that a nitrogen sweep of the reaction vessel headspace facilitated removal of trimethylamine, which is a degradation-product of trimethylamine N-oxide.

Removal of trimethylamine in this fashion was found to advantageously achieve consistently high yields of buprenorphine product, with low impurity levels.

Example 9

Demethylation of 3-O-methyl-N-methylbuprenorphine

Reaction Scheme for Examples 9 and 10

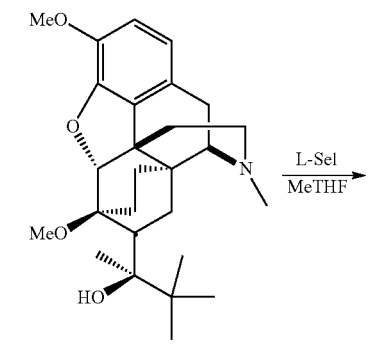

3-O-methyl-N-methylbuprenorphine

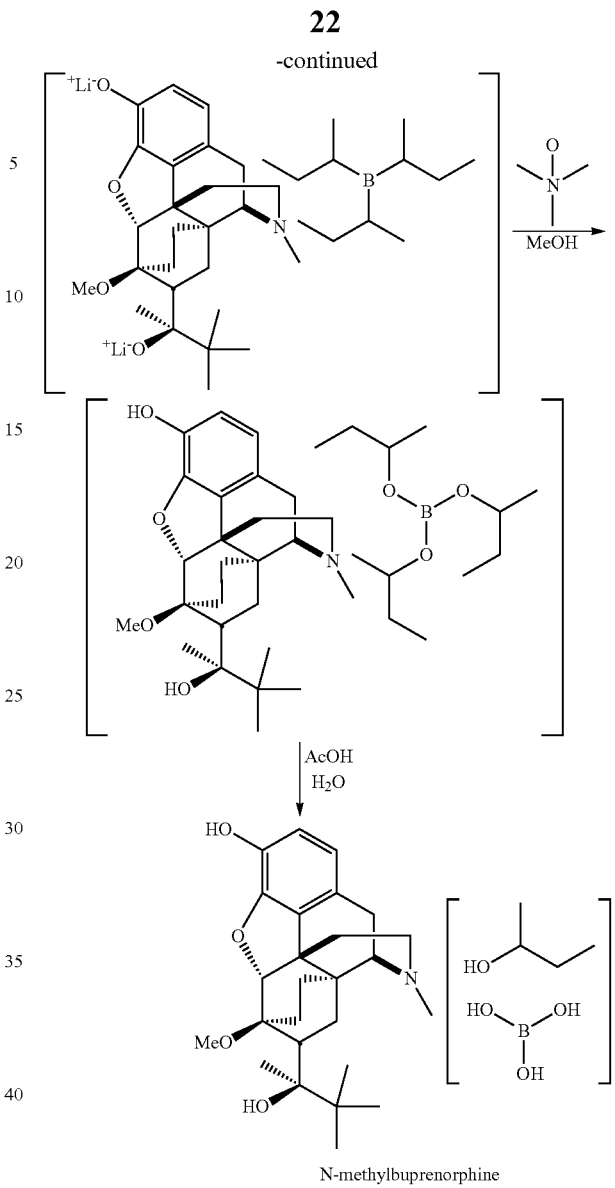

N-methylbuprenorphine

Under a $N_2$ atmosphere, a mixture of 3-O-methyl-N-methylbuprenorphine (9.2 g, 20.8 mmol) and MeTHF (30 mL) was heated to 40° C. and treated with a mixture of LiBr (3.2 g, 36.5 mmol) in MeTHF (16 mL), followed by lithium tri-sec-butylborohydride (L-Selectride® 1 M in THF, 58 mL, 58 mmol) via syringe. The charge was exothermic reaching 50° C. with gas evolution. The reaction mixture was then heated to 70° C. for 16 h, at which time it was found that 0.1% of the 3-O-methyl-N-methylbuprenorphine remained (according to UPLC). The mixture was heated to 90° C. and 53 mL of solvent was collected. The resultant mixture was cooled to 60° C. and used in Example 10 without further purification.

Example 10

Isolation of N-methylbuprenorphine

The N-methylbuprenorphine mixture of Example 9 was treated with a solution of TMO dihydrate (27.2 g, 245 mmol) in MeOH (30 mL). An exotherm, with gas evolution, was observed. The reaction mixture was then heated under reflux and 30 mL of solvent was distilled off, and then allowed to cool to 25° C. upon which a slurry was formed.

The mixture was treated with water (46 mL), followed by AcOH until the mixture reached pH 7. Phase separation occurred and the two-phase mixture was stirred for 16 h. MTBE (50 mL) was added and the mixture was stirred at 50° C. The phases were separated and the organic phase collected. The aqueous phase was washed with MTBE (25 mL) and the combined organic phases were concentrated and triturated with MTBE. The resultant slurry was treated with NH$_4$OH (200 mL), and the phases were allowed to separate.

The resultant precipitate in the organic phase was collected by filtration to afford N-methylbuprenorphine (1.10 g, 2.52 mmol, 12% yield). The organic phase was collected and concentrated to afford a second crop of N-methylbuprenorphine (2.40 g, 27% yield).

The solids were analysed by UPLC/MS and $^1$H NMR.

Example 11

Demethylation of 3-O-methyl-norbuprenorphine

Reaction Scheme for Examples 11 and 12

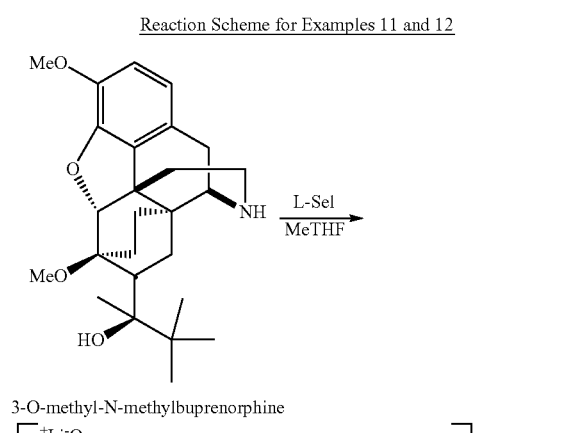

3-O-methyl-N-methylbuprenorphine

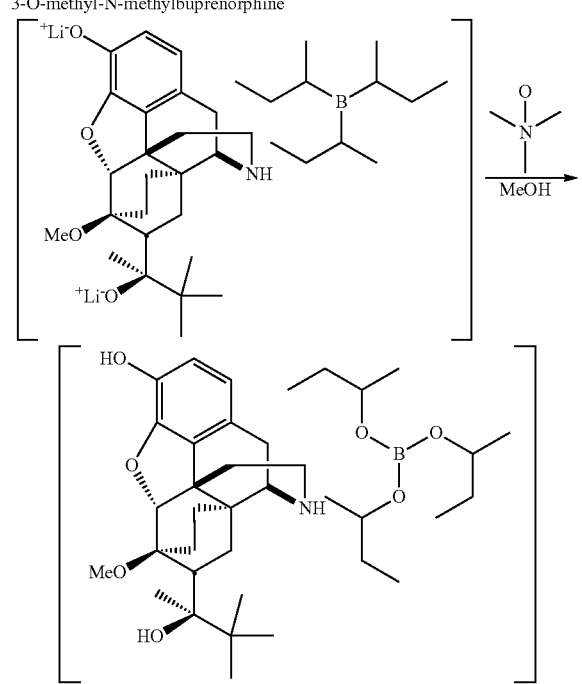

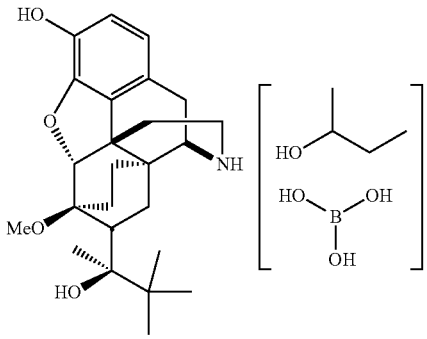

Norbuprenorphine

Under a N$_2$ atmosphere, a mixture of 3-O-methyl-norbuprenorphine (2.48 g, 5.8 mmol) and MeTHF (22.5 mL) was heated to 40° C. and treated with LiBr (0.88 g, 10.2 mmol). The mixture was heated to 50° C. and treated with lithium tri-sec-butylborohydride (L-Selectride® 1 M in THF, 16.2 mL, 16.2 mmol) via syringe. The reaction mixture was then heated to 70° C. and stirred for 16 h. UPLC analysis showed that 5.2% of 3-O-methyl-norbuprenorphine remained, and the mixture was treated with further lithium tri-sec-butylborohydride (L-Selectride® 1 M in THF, 1.5 mL, 1.5 mmol) and stirred for 20 h. A sample was obtained and analysed by UPLC showing full conversion to norbuprenorphine. The mixture was cooled to 20° C. and used in Example 12 without further purification.

Example 12

Isolation of Norbuprenorphine

The norbuprenorphine mixture of Example 11 was treated with a solution of TMO dihydrate (7.58 g, 68.0 mmol) in MeOH (9 mL). An exotherm, with gas evolution, was observed. The reaction mixture was then heated at 60° C. for 1 h. The resultant white slurry was cooled to 20° C. After 12 h, the mixture was heated to 80° C. and 14 mL of solvent was distilled off, and then the mixture was allowed to cool to 20° C.

The mixture was treated with water (5 mL), followed by AcOH until the mixture reached pH 7. The phases were separated, and the organic phase was treated with MTBE and sonicated. The resultant precipitate was collected by filtration to afford norbuprenorphine (1.19 g, 2.87 mmol, 50% yield). The solids were analysed by UPLC/MS and $^1$H NMR.

Example 13

Demethylation of 3-O-methyl-buprenorphine to Buprenorphine Using NMO

Acetonitrile (20 mL) and K$_3$PO$_4$ (7.48 g, 35.0 mmol) were charged to a jacketed European flask under N$_2$ atmosphere. 3-O-methyl-norbuprenorphine (3.35 g, 7.80 mmol) and bromomethylcyclopropane (1.60 g, 12.0 mmol) were subsequently charged to the slurry. The reaction mixture was heated to 60.0° C. for 40 h when a sample was pulled for UPLC/MS analysis. The analysis showed full conversion to 3-O-methylbuprenorphine. The reaction mixture was cooled to 40.0° C. MTBE (25 mL) and water (25 mL) were added and the mixture stirred for 10 minutes. The agitation was stopped and the phases were allowed to separate. The aqueous phase was discarded.

The jacket was incrementally set to 75.0° C. for distillation and 15 mL of distillate was collected. MeTHF (25 mL) was added and the distillation was continued. 15 mL of distillate was collected (pot temperature 70.8° C.), then reaction was cooled to 20° C. and held under a $N_2$ atmosphere for 22 h. LiBr (1.45 g, 2.13 mmol) and MeTHF (25 mL) were charged to the flask. The mixture was heated for distillation (pot temperature 76° C.) and 25 mL of distillate collected. MeTHF (25 mL) was added, followed by an additional addition of MeTHF (25 mL). The distillation was continued (pot temperature 82.1° C.) and 25 mL of distillate was collected.

The resulting mixture was cooled to 30.0° C. and a 1 M L-Selectride solution in THF (31.5 mL, 31.0 mmol) was added by the means of a syringe to the mixture. The first 10 mL produced off gassing, but no exotherm. The jacket was heated in stages to 110.0° C. to allow for distillation. Distillation was started at a pot temperature of 74.9° C. 35 mL of a distillate had been collected when the pot temperature reached 98.0° C. A sample was pulled and analyzed by UPLC showing that 15.0% of 3-O-methyl-buprenorphine remained. The reaction was further heated for 2 hours at 98.0° C. then a sample was pulled and analyzed by UPLC showing full conversion to buprenorphine.

The reaction mixture was cooled to 15.0° C. and MeOH (3 mL) was added dropwise. The addition produced gas evolution with an initial exotherm. The temperature rose from 15.0 to 20° C. The heater/chiller was turned off and the reaction mixture was stirred at ambient temperature for 16 h. A 50% solution of 4-methylmorpholine N-oxide (24.4 mL, 118.0 mmol) was added slowly by the means of a syringe. The addition produced an exotherm (19.0° C. to 27.0° C.). The exotherm subsided after 5 mL of the 50% solution of 4-methylmorpholine N-oxide had been added. The mixture was heated to 40.0° C. for 18 h. Water (15 mL) was added to the cloudy mixture and the pH was measured to ~13 by pH paper in the aqueous layer. L-tartaric acid (2.40 g, 16.0 mmol) was added and the resulting mixture stirred for 10 minutes. pH was measured to ~9 in the lower aqueous layer. The agitation was stopped and the phases were allowed to separate. The aqueous phase was discarded. Water (15 mL) was added to the mixture. Agitation was stopped after 10 minutes and the phases were allowed to separate.

The pH of the discarded aqueous phase was ~9. The organic phase was treated with water (15 mL), NaCl (1.5 g, 26.0 mmol) and L-tartaric acid (0.12 g, 1.0 mmol). The mixture was stirred for 10 minutes. The agitation was stopped and the phases were allowed to separate. The aqueous phase was discarded.

Acetonitrile (25 mL) was added to the reaction giving a light yellow slurry. The jacket was set to 90° C. for distillation. The distillation started when the pot temperature reached 77.7° C. and 25 mL distillate was collected. Acetonitrile (25 mL) was charged. The pot temperature reached 83.8° C. and 25 mL distillate was collected. Acetonitrile (25 mL) was charged for a third time. The pot temperature reached 83.4° C. and 25 mL of distillate was collected. Acetonitrile (25 mL) was charged for a fourth time. The final pot temperature was 82.8° C. and 20 mL distillate was collected. The jacket was shut off and the reaction slurry held at ambient temperature for 17 h. The jacket was set to 5.0° C. and aged for 1 h.

The solids were filtered off by suction filtration. The wet cake was washed with acetonitrile (25 mL) and suction dried on the filter to give buprenorphine (1.77 g, 3.8 mmol, 48% yield).

The combined solids were analyzed by UPLC/MS and $^1$H NMR. The purity profile by UPLC/MS is shown in Table 3.

TABLE 3

| purity profile | | | |
|---|---|---|---|
| 3-O-methyl-buprenorphine | Norbuprenorphine | Buprenorphine | Others |
| 0.45 | 0.26 | 99.07 | 0.23[1] |

[1] 0.13% butyl-buprenorphine and 0.10% bupreneorphine-carbinolamine.

Example 14

Demethylation of 3-O-methyl-buprenorphine without any Oxidant Present

3-O-methyl-norbuprenorphine (10.0 g, 16.0 mmol) and $K_3PO_4$ (11.7 g, 55.0 mmol) were charged to a jacketed European flask under $N_2$ atmosphere. Acetonitrile (40 mL)) and bromomethylcyclopropane (3.20 g, 24.0 mmol) were subsequently charged to the slurry. The reaction mixture was heated to 40.0° C. for 19 h when a sample was pulled for UPLC/MS analysis (Table 4, entry 1). The analysis showed 97% conversion to 3-O-methylbuprenorphine. Bromomethylcylopropane (0.64 g, 5.0 mmol) was added to the reaction mixture. The reaction mixture was stirred for an additional 3 h. A sample was pulled for UPLC/MS analysis (Table 4, entry 2) showing 99.0% conversion to 3-O-methylbuprenorphine. Water (50 mL) was charged to the mixture. The circulator was set to 99.0° C. and the flask was equipped with a short path distillation head. 45 mL was distilled off and the mixture was cooled to 30.0° C. The mixture contained a big yellow lump which was dissolved upon treatment with MTBE (50 mL). The agitation was stopped and the phases were allowed to separate. The aqueous phase was discarded. Water (50 mL) was added to the organic phase and the mixture stirred for 5 min. The agitation was stopped and the phases were allowed to separate. The aqueous phase was discarded.

The circulator was set to 70.0° C. and the flask was again equipped with a short path distillation head. 26 mL of distillate was collected, then toluene (30 mL) and LiBr (5.5 g, 63.0 mmol) was added to the flask. The LiBr was observed to be caking on the walls and in the bottom of the flask. The temperature of the circulator was set to 107.0° C. 24 mL distillate was collected at 95.1° C. Toluene (30 mL) was charged to the pot. The pot temperature was gradually raised to 110.9° C. and 31 mL of distillate was collected. Toluene (50 mL) was charged to the pot. The LiBr was now a free-flowing solid in the flask. The distillation was continued and 21 mL was collected. The final pot temperature was 111.0° C. The reaction mixture was cooled to 20.0° C. and held at 20.0° C. for 94 h. Toluene (25 mL) was charged to the reaction mixture. The resulting mixture was heated for distillation and 36 mL was collected. The internal temperature of the mixture was 110.8° C. The reaction mixture was cooled to 23.8° C. and a 1 M L-Selectride solution in THF (2.0 mL, 2.0 mmol) was added by the means of a syringe to the mixture. The temperature rose from 23.8° C. to 24.3° C. and effervescence was observed during the addition. Additional 1 M L-Selectride solution in THF (3.0 mL, 3.0 mmol) was charged. The internal temperature increased to 24.7° C.

Additional 1 M L-Selectride solution in THF (2.0 mL, 2.0 mmol) was charged with continued off gassing during the addition. The temperature increased to 25.2° C. Additional 1 M L-Selectride solution in THF was charged (3.0 mL, 3.0 mmol) was charged with no observable exotherm, but effervescence was still observed during the addition. Additional 1 M L-Selectride solution in THF was charged (10.0 mL, 10.0 mmol) was charged with no observable exotherm and effervescence was still observed during the addition. Additional 1 M L-Selectride solution in THF was charged (5.0 mL, 5.0 mmol) was charged with no observable exotherm but effervescence was still observed during the addition. Additional 1 M L-Selectride solution in THF was charged (15.0 mL, 15.0 mmol) and effervescence was still observed during the addition. Additional 1 M L-Selectride solution in THF was charged (6.0 mL, 6.0 mmol) and effervescence was still observed during the addition. Additional 1 M L-Selectride solution in THF was charged (5.0 mL, 5.0 mmol) and effervescence was still observed during the addition. Additional 1 M L-Selectride solution in THF was charged (10.0 mL, 10.0 mmol). No effervescence was observed during the addition. Additional 1 M L-Selectride solution in THF was charged (20.0 mL, 20.0 mmol). The reaction mixture was heated to a gentle reflux at 81.8° C. A sample was pulled after 16 h (Table 4, entry 3) which was analyzed by UPLC/MS showing 98.8% conversion to buprenorphine. A sample was pulled after 21 h (Table 4, entry 4) which was analyzed by UPLC/MS showing 98.8% conversion to buprenorphine, 0.2% remaining 3-O-methylbuprenorphine and 1.0% norbuprenorphine. The reaction was cooled to 15° C. 10% aq. acetic acid (1 mL) was added. The addition was exothermic with considerable effervescence. Additional 10% aq. acetic acid (1 mL) was charged. The addition was exothermic with considerable effervescence. Additional 10% aq. acetic acid was charged in portions, with no observable effervescence but the exotherm remained throughout these additions. In total 28 mL of 10% acetic acid was charged. The pH was ~14 in the reaction mixture.

The reaction mixture was heated to 40° C. and additional 10% aq. acetic acid (10 mL) was charged in portions. The agitation was stopped and the phases were allowed to separate. The aqueous phase (30 mL) was discarded. A sample was pulled from the organic phase (Table 4, entry 5) which was analyzed by UPLC/MS. Additional water (25 mL) was charged to the organic phase. The phases were stirred for 5 min. The stirring was stopped and the phases were allowed to separate. The aqueous phase (32 mL) was discarded. The pH in the aqueous phase was ~13.

The reaction flask was equipped with a short path distillation head and heated for distillation. Distillate was starting to collect at an internal temperature of 71.8° C. In total 75 mL was collected when the internal temperature had reached 97° C. The reaction was cooled and kept at 20.0° C. for 17 h. Water (50 mL) was charged and the reaction was heated for distillation. The reaction mixture was refluxing at 81.7° C. and at 84.0° C. a sudden event of off gassing occurred. The off gassing was associated with the formation of a considerable amount of foam. The total volume of distillate collected was 38 mL. Water (50 mL) was added and 40 mL of distillate was collected. The final temperature of the reaction mixture was 98.9° C. The reaction mixture was cooled to 37.1° C. The agitation was stopped and the phases were allowed to separate. The volume of the upper milky layer was 20 mL. The volume of the lower aqueous layer was 20 mL. The pH of the aqueous layer was ~9. MTBE (50 mL) was added to the reaction mixture. The resulting mixture was stirred for 5 min. The stirring was stopped and the phases were allowed to separate. A sample was pulled from the organic phase (Table 4, entry 6) which was analyzed by UPLC/MS. The milky aqueous layer (60 mL) was discarded. The pH of the aqueous layer was ~13. Water (50 mL) was added to the organic phase. The resulting mixture was stirred for 15 min. The agitation was stopped and the phases were allowed to separate. The clear aqueous layer (50 mL) was discarded. The pH of the aqueous layer was ~9. Water (50 mL) was added to the organic phase. The resulting mixture was stirred for 15 min. The agitation was stopped and the phases were allowed to separate. The clear aqueous layer (50 mL) was discarded. The pH of the aqueous layer was ~7.

Acetonitrile (50 mL) was charged to the reaction mixture. The reaction mixture was heated for distillation. The reaction mixture reached 70.0° C. A total volume of 40 mL of distillate was collected. The reaction mixture reached 70.0° C. Additional acetonitrile (50 mL) was added and the distillation continued. 54 mL of distillate had been collected when the reaction mixture temperature reached 81.5° C. Additional acetonitrile (50 mL) was added and the distillation continued. 60 mL of distillate had been collected when the reaction mixture temperature reached 81.5° C. The reaction mixture was a slurry at this point. The reaction mixture was cooled to 20° C. and held for 16 h. The solids were filtered off to and air dried on a petri dish to give 3.6 g, 7.7 mmol. The solids were analyzed by UPLC/MS (Table 4, entry 7). A sample was pulled from the mother liquor (Table 4, entry 8) which was analyzed by UPLC/MS.

The reaction profile and the purity profile for the wet cake analyzed by UPLC/MS is shown in Table 4.

TABLE 4

The reaction profile and the purity profile for the wet cake analyzed by UPLC/MS

| Entry | IPC (h) | 3-O-Me-buprenorphine (Area %) | Norbuprenorphine (Area %) | Buprenorphine (Area %) | Others (Area %) |
|---|---|---|---|---|---|
| 1 | 19 | 97.12 | | | 4.88[1] |
| 2 | 24 | 98.96 | | | 1.04[1] |
| 3 | 16 | 0.22 | 0.93 | 98.85 | |
| 4 | 21 | 0.05 | 0.86 | 99.09 | |
| 5 | | | 0.94 | 99.06 | |
| 6 | | | 2.82 | 96.88 | 0.30 |
| 7 | | | 0.33 | 98.79 | 0.88 |
| 8 | | | 10.13 | 85.55 | 4.32 |

[1]3-O-methylnorbuprenorphine

Example 15

Demethylation of 3-O-methyl-buprenorphine without Initial Oxidant Quench

3-O-methyl-norbuprenorphine (3.35 g, 7.80 mmol) and acetonitrile (20 mL) were charged to a jacketed European flask under $N_2$ atmosphere. $K_3PO_4$ (6.62 g, 31.0 mmol) and bromomethylcyclopropane (1.60 g, 12.0 mmol) were subsequently charged to the slurry. The reaction mixture was heated to 50.0° C. for 42 h when a sample was pulled for UPLC/MS analysis. The analysis showed full conversion to 3-O-methylbuprenorphine. The reaction mixture was cooled to 40.0° C. MeTHF (25 mL) and water (25 mL) were added and the mixture stirred for 10 min. The agitation was stopped and the phases were allowed to separate. Water (25 mL) was added to the organic phase and the mixture stirred for 10 min. The agitation was stopped and the phases were allowed to separate. A sample was pulled from both of the aqueous phases which showed the presence of 3-O-methylbuprenorphine. The aqueous phases were pooled and re-extracted with MTBE (25 mL). The aqueous phase was discarded and the organic phases were pooled.

The jacket was incrementally set to 70.0° C. for distillation and 39 mL of distillate was collected at 61.0° C. MeTHF (25 mL) was added and the distillation was continued. 28 mL of distillate was collected. The pot temperature reached 69.8° C. during this distillation.

MeTHF (25 mL) was added and the distillation was continued. 28 mL of distillate was collected and the pot temperature was 78.7° C. MeTHF (25 mL) was added and the distillation was continued. 20 mL of distillate was collected. The pot temperature reached 79.7° C. during this distillation. The reaction mixture was cooled to 20° C., LiBr (1.40 g, 16.0 mmol) and MeTHF (25 mL) were charged to the flask. The mixture was heated for distillation. The pot temperature reached 80.3° C. and 24.5 mL of distillate was collected.

The resulting mixture was cooled to 25° C. and a 1 M L-Selectride solution in THF (35.5 mL, 35.0 mmol) was added by the means of a syringe to the mixture. The first 10 mL produced off gassing, but no exotherm. The jacket was heated in stages to 105.0° C. to allow for distillation. Distillation was starting when the pot temperature reached 74.5° C. 26 mL of a distillate had been collected when the pot temperature had reached 90.9° C., then a sample was pulled (Table 5, entry 1) which was analyzed by UPLC/MS. The reaction was further heated for 2 hours at 102.0° C., then an additional sample was pulled (Table 5, entry 2) which was analyzed by UPLC/MS showing full conversion to buprenorphine.

The reaction mixture was cooled to 15.0° C. A sample was pulled from the organic phase (Table 5, entry 3) and 20% aq. acetic acid (1 mL) was added dropwise. The addition produced gas evolution and an exotherm evolved from 14° C. to 23.5° C. The remaining 20% aq. acetic acid (9 mL) was added in one portion. No effervescence observed but the temperature rose to 33.0° C. The pH was adjusted to 9 and MTBE (14 mL) was added. The mixture was stirred for 10 min. The agitation was stopped and the phases were allowed to separate. The cloudy aqueous phase was discarded. MTBE (5 mL) was charged to the organic phase, followed by water (25 mL). The mixture was stirred for 5 min, then the agitation was stopped. The phases were allowed to separate and the aqueous phase was discarded. It was observed that the aqueous phase was less cloudy. Water (25 mL) was charged to the organic phase and the resulting mixture was stirred for 4 min. The agitation was stopped and the phases were allowed to separate. The aqueous phase was discarded. A sample was pulled from the organic phase (Table 5, entry 4).

A 50% solution of 4-methylmorpholine N-oxide (25.0 mL, 121 mmol) was added to organic phase. The resulting mixture was heated to 44.0° C. for 1 h. The agitation was stopped and the phases were allowed to separate. The aqueous phase was discarded. Water (25 mL) was charged to the organic phase. The resulting mixture was stirred for 7 min, then the agitation was stopped. The phases were allowed to separate. The aqueous phase was discarded. A sample was pulled from the organic phase (Table 5, entry 5).

Acetonitrile (25 mL) was added to the organic phase and the reaction mixture heated for distillation. 23 mL of distillate was collected. Acetonitrile (25 mL) was added to the mixture. The distillation was continued. Additional acetonitrile (25 mL) was charged when 32 mL of distillate had been collected. Acetonitrile (25 mL) was charged and the distillation continued until 26 mL of distillate had been collected. Acetonitrile (25 mL) was charged for a final time and 24 mL of distillate was collected. The reaction mixture was cooled to 5.0° C. and stirred for 18 h. The formed solids were filtered off and suction dried on the filter. The solids were analyzed by UPLC/MS (Table 5, entry 6).

The reaction profile and the purity profile for the wet cake analyzed by UPLC/MS is shown in Table 5.

TABLE 5

The reaction profile and the purity profile for the wet cake analyzed by UPLC/MS

| Entry | Norbuprenorphine (Area %) | Buprenorphine (Area %) | Others (Area %) |
|---|---|---|---|
| 1 | 0.14 | 98.98 | 0.88[1] |
| 2 | 0.10 | 99.90 | |
| 3 | | 100 | |
| 4 | 20.08 | 78.79 | 1.13 |
| 5 | 20.19 | 79.48 | 0.33 |
| 6 | 19.76 | 79.58 | 0.66 |

[1]3-O-methylbuprenorphine.

The performance of an initial aqueous quench of the borohydride reaction mixture (using 20% aq. acetic acid) without prior or simultaneous oxidation of the trialkylborane leads to the formation of relatively high levels of norbuprenorphine.

ABBREVIATIONS

AcOH Acetic acid

AMBH Alkali metal borohydride

Aq. Aqueous

Bup Buprenorphine

CPM-Br (Bromomethyl)cyclopropane

Eq. Molar equivalent

Δ Reflux temperature

HPLC High performance liquid chromatography hr Hours

IPA Isopropyl alcohol

LS L-Selectride®

2-MeTHF 2-Methyltetrahydrofuran

MeOH Methanol

MeCN Acetonitrile min Minutes

MTBE tert-Butyl methyl ether

NMO N-Methylmorpholine N-oxide norBup Norbuprenorphine

3OMB 3-O-methyl-buprenorphine

3OMnB 3-O-methyl-norbuprenorphine ppm parts per million

SH Superhydride

TFA Trifluoroacetic acid

THF Tetrahydrofuran

TMO Trimethylamine N-oxide

TSBB Tri-sec-butyl borane

UPLC/MS Ultra performance liquid chromatography-mass spectrometry

The invention claimed is:
1. A process for the preparation of a compound of formula I,

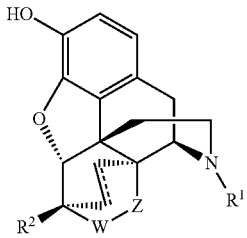

or a pharmaceutically acceptable salt thereof;
wherein:
W and Z independently represent $CHR^3$ or S, provided that at least one of W and Z represents $CHR^3$;
$R^1$ represents hydrogen, $C_{1-12}$ alkyl, $C_{2-12}$ alkenyl, $C_{2-12}$ alkynyl or $C_{3-12}$ cycloalkyl (which latter four groups are optionally substituted by one or more substituents selected from the list consisting of halogen atoms, phenyl groups and $C_{3-12}$ cycloalkyl groups);
$R^2$ represents hydrogen, a halogen atom, $-OR^4$, $-OC(O)R^4$, $-N(R^4)_2$, $C_{1-12}$ alkyl, $C_{2-12}$ alkenyl or $C_{2-12}$ alkynyl (which latter three groups are optionally substituted by one or more halogen atoms);
each $R^3$ independently represents hydrogen, $-CN$, $C_{1-12}$ alkyl, $C_{2-12}$ alkenyl, $C_{2-12}$ alkynyl or $C_{3-12}$ cycloalkyl (which latter four groups are optionally substituted by one or more substituents selected from the list consisting of halogen atoms, $-OR^5$ groups and 5 to 10-membered heteroaryl groups);
$R^4$ independently represents hydrogen, $C_{1-6}$ alkyl, $C_{3-6}$ cycloalkyl, $C_{6-10}$ aryl (which latter three groups are optionally substituted by one or more halogen atoms or phenyl groups);
$R^5$ represents hydrogen or $C_{1-6}$ alkyl, optionally substituted by one or more halogen atoms; and
⫤ represents a single or double bond;
which process comprises contacting a compound of formula II,

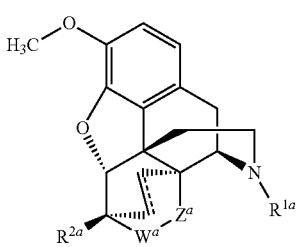

or a salt thereof,
wherein $R^{1a}$, $R^{2a}$, $W^a$ and $Z^a$ are defined according to $R^1$, $R^2$, W and Z, respectively, with an alkali metal borohydride and an additional alkali metal salt.

2. The process of claim 1, wherein: (i) $R^1$ represents methyl, ethyl, propyl, butyl, benzyl or $-CH_2$-cyclopropyl; or (ii) $R^3$ represents $C_{1-6}$ alkyl optionally substituted by one or more substituents selected from the group consisting of halogen atom, $-OR^5$ groups, 5-membered heteroaryl groups.

3. The process of claim 1, wherein W and Z independently represent $CHR^3$, and optionally, wherein W represents $CHR^3$ and Z represents $CH_2$.

4. The process of claim 2, wherein $R^3$ represents $C_{1-6}$ alkyl optionally substituted by one or more substituents selected from the list consisting of $-OH$ and thiophenyl.

5. The process of claim 4, wherein $R^3$ represents:

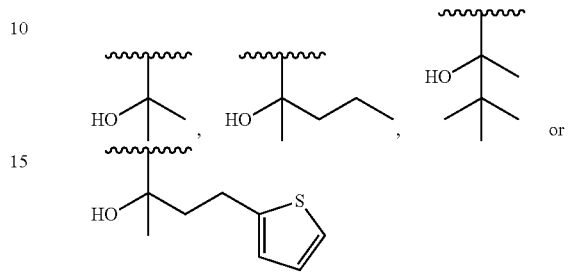

wherein ⁓ represents the point of attachment of $R^3$ to the rest of the compound of formula I.

6. The process of claim 1, wherein:
(i) wherein $R^2$ represents $-OR^4$; $-OC(O)R^4$; or a methoxy group;
(ii) the alkali metal borohydride and the additional alkali metal salt each comprise the same alkali metal; or
(iii) the alkali metal borohydride is a compound of formula III,

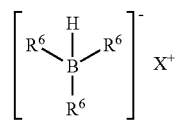

wherein each $R^6$ independently represents $C_{1-12}$ alkyl, and $X^+$ represents an alkali metal cation.

7. The process of in claim 6, wherein the alkali metal borohydride is an alkali metal tri-sec-butylborohydride or an alkali metal trisiamylborohydride; and optionally, wherein (i) the alkali metal borohydride is lithium tri-sec-butylborohydride or (ii) the amount of alkali metal borohydride present is from about 1 to about 10 equivalents relative to the compound of formula II.

8. The process of claim 7, wherein: (i) the amount of alkali metal borohydride present is from about 2 to about 5 equivalents relative to the compound of formula II; or (ii) the additional alkali metal salt is lithium bromide; and optionally, wherein the additional alkali metal salt contains from about 1 to about 6 equivalents of alkali metal cations relative to the compound of formula II.

9. The process of claim 1, wherein: (i) the additional alkali metal salt is lithium bromide; or (ii) wherein the additional alkali metal salt is an alkali metal halide.

10. The process of claim 1, wherein the additional alkali metal salt contains from about 1.5 to about 3 equivalents of alkali metal cations relative to the compound of formula II and optionally, wherein: the reaction is performed in a solvent system comprising 2-methyltetrahydrofuran.

11. The process of claim 1, wherein: (a) wherein the reaction is performed at a temperature of up to about 150° C.; or (b) the compound of formula I is buprenorphine and the process comprises contacting 3-O-methyl-buprenorphine with:

(i) an alkali metal borohydride selected from the group consisting of lithium tri-sec-butylborohydride, sodium tri-sec-butylborohydride, potassium tri-sec-butylborohydride, and mixtures thereof; and
(ii) an additional alkali metal halide.

12. The process of claim 1, wherein the process further comprises adding an oxidant after the compound of formula I has been formed and optionally, wherein the oxidant is an amine N-oxide, and/or the amine N-oxide is selected from the list consisting of trimethylamine N-oxide and N-methylmorpholine N-oxide.

13. The process of claim 12, wherein the amount of oxidant added is from about 1 to about 10 equivalents relative to the total amount of alkali metal borohydride added to the reaction mixture.

14. The process of claim 13, wherein the amount of oxidant added is from about 3 to about 7 equivalents relative to the alkali metal borohydride.

15. The process of claim 1, wherein the compound of formula II is formed by a process comprising reacting a compound of formula IV,

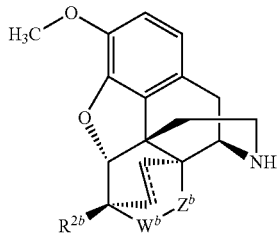

IV or a salt thereof,
wherein $R^{2b}$, $W^b$ and $Z^b$ are defined according to $R^2$, W and Z, respectively, with a compound of formula V, $R^7$—Y      V wherein:
$R^7$ represents $C_{1-12}$ alkyl, $C_{2-12}$ alkenyl, $C_{2-12}$ alkynyl or $C_{3-12}$ cycloalkyl, which groups are optionally substituted by one or more substituents selected from the list consisting of halogen atoms, phenyl groups and $C_{3-12}$ cycloalkyl groups; and
Y represents a suitable leaving group and optionally, wherein (i) wherein: $R^7$ represents methyl, ethyl, propyl, butyl, benzyl or —$CH_2$-cyclopropyl; and Y represents chloro, bromo, iodo, mesylate or tosylate; or (ii) the reaction between the compound of formula IV and the compound of formula V is conducted in the presence of an inorganic base.

16. The process of claim 15, wherein the compound of formula IV is 3-O-methyl-norbuprenorphine, and the compound of formula II is 3-O-methyl-buprenorphine.

17. A process for preparing a pharmaceutically acceptable salt of a compound of formula I, as defined in claim 1, which process comprises the steps of:
(i) preparing a compound of formula I in accordance with a process as claimed in claim 1;
(ii) optionally isolating and/or purifying the compound of formula I obtained from that process;
(iii) bringing into association the compound of formula I so formed with an acid;
(iv) optionally wherein the product of step (iii) is converted into a different salt.

18. A process for preparing a pharmaceutical formulation comprising a compound of formula I, or a pharmaceutically acceptable salt thereof, as defined in claim 1, which process comprises the steps of:
(i) preparing a compound of formula I (or pharmaceutically acceptable salt thereof) in accordance with the process of claim 1;
(ii) optionally isolating and/or purifying the compound of formula I (or pharmaceutically acceptable salt thereof) obtained from that process; and
(iii) bringing into association the compound of formula I so formed (or pharmaceutically acceptable salt thereof) with one or more pharmaceutically acceptable excipients, adjuvants, diluents or carriers.

19. A process for the preparation of buprenorphine, or a pharmaceutically acceptable salt thereof, wherein the process comprises the steps of:
(i) contacting 3-O-methyl-buprenorphine with an alkali metal borohydride; and
(ii) adding an oxidant to the mixture obtained in (i).

* * * * *